(12) United States Patent
Nicolette et al.

(10) Patent No.: US 8,513,208 B2
(45) Date of Patent: Aug. 20, 2013

(54) TRANSIENT EXPRESSION OF IMMUNOMODULATORY POLYPEPTIDES FOR THE PREVENTION AND TREATMENT OF AUTOIMMUNE DISEASE, ALLERGY AND TRANSPLANT REJECTION

(75) Inventors: Charles A. Nicolette, Durham, NC (US); C. Garrison Fathman, Portola Valley, CA (US); Remi Creusot, San Francisco, CA (US)

(73) Assignees: Argos Therapeutics, Inc., Durham, NC (US); The Board of Trustees of the Leland Stanford Junior University, Palo Alto, CA (US)

( * ) Notice: Subject to any disclaimer, the term of this patent is extended or adjusted under 35 U.S.C. 154(b) by 66 days.

(21) Appl. No.: 12/735,932

(22) PCT Filed: Feb. 27, 2009

(86) PCT No.: PCT/US2009/001232
§ 371 (c)(1),
(2), (4) Date: Nov. 10, 2010

(87) PCT Pub. No.: WO2009/108341
PCT Pub. Date: Sep. 3, 2009

(65) Prior Publication Data
US 2011/0081327 A1    Apr. 7, 2011

Related U.S. Application Data

(60) Provisional application No. 61/067,459, filed on Feb. 28, 2008.

(51) Int. Cl.
*C07H 21/02* (2006.01)
*C12Q 1/68* (2006.01)

(52) U.S. Cl.
USPC .............................. 514/44; 536/23.1; 435/6.1

(58) Field of Classification Search
None
See application file for complete search history.

(56) References Cited

U.S. PATENT DOCUMENTS

| | | | |
|---|---|---|---|
| 6,670,186 B1 | 12/2003 | Nair et al. | |
| 7,378,089 B2 * | 5/2008 | Fathman | 424/93.71 |
| 2003/0091548 A1 | 5/2003 | Fathman | |
| 2007/0082400 A1 | 4/2007 | Healey et al. | |
| 2010/0291084 A1 * | 11/2010 | Kopf et al. | 424/135.1 |

FOREIGN PATENT DOCUMENTS

| | | |
|---|---|---|
| WO | 97/26325 A1 | 7/1997 |
| WO | WO 02/088346 | 11/2002 |
| WO | 03/045318 * | 6/2003 |
| WO | 03045318 A2 | 6/2003 |
| WO | WO 2007/096278 | 8/2007 |

OTHER PUBLICATIONS

Cameron et al., "IL-4 Prevents Insulitis and Insulin-Dependent Diabetes Mellitus in Nonobese Diabetic Mice by Potentiation of Regulatory T Helper-2 Cell Function" *J. Immunology* vol. 159, pp. 4686-4692 (1997).
Feili-Hariri et al., "Dendritic Cells Transduced to Express Interleukin-4 Prevent Diabetes in Nonobese Diabetic Mice with Advanced Insulitis" *Human Gene Therapy* vol. 14, pp. 13-23 (2003).
Piccirillo et al., "Prevention of experimental allergic encephalomyelitis by intramuscular gene transfer with cytokine-encoding plasmid vectors" *Hum Gene Ther* vol. 10, pp. 1915-1922 (1999).
Bessis et al., "Syngeneic fibroblasts transfected with a plasmid encoding interleukin-4 as non-viral vectors for anti-inflammatory gene therapy in collagen-induced arthritis" *J. Gene Med* vol. 4, pp. 300-307 (2002).
King et al., "TGF-beta1 alters APC preference, polarizing islet antigen responses toward a Th2 phenotype" *Immunity* vol. 8, pp. 601-613 (1998).
Perone et al., "Dendritic cells expressing transgenic galectin-1 delay onset of autoimmune diabetes in mice" *J. Immunol.* vol. 177, pp. 5278-5289 (2006).
Smith et al., "Localized expression of an anti-TNF single-chain antibody prevents development of collagen-induced arthritis" *Gene Ther.* vol. 10, pp. 1248-1257 (2003).
Creusot et al., "A short pulse of Il-4 delivered by DCs electroporated with modified mRNA can both prevent and treat autoimmune diabetes in NOD mice" *Mol. Ther.* vol. 18, No. 12, pp. 2112-2120 (Dec. 2010).
Falcone et al., "IL-4 triggers autoimmune diabetes by increasing self-antigen presentation within the pancreatic islets" *Clin Immunol.* vol. 98, No. 2, pp. 190-199 (Feb 2001).
Tominaga et al., "Administration of Il-4 prevents autoimmune diabetes but enhances pancreatic insulitis in NOD mice" *Clin Immunol. Immunopathol.* vol. 86, No. 2, pp. 209-218 (Feb. 1998).
Arreaza et al., "Neonatal Activation of Cd28 Signaling Overcomes T Cell Anergy and Prevents Autoimmune Diabetes by an IL-4-dependent Mechanism" *J. Clin. Invest.* vol. 100, No. 9, pp. 2243-2253 (Nov. 1997).
Cameron, et al., "Biolistic-Mediated Interleukin 4 Gene Transfer Prevents the Onset of Type 1 Diabetes" *Human Gene Therapy* vol. 11, pp. 1647-1656 (Aug. 10, 2000).
Cameron, et al., "Immunotherapy of spontaneous type 1 diabetes in nonobese diabetic mice by systemic interleukin-4 treatment employing adenovirus vector-mediated gene transfer" *Gene Therapy* Vo. 7, pp. 1840-1846. (2000).
Chang et al., "Intramuscular Administration of Expression Plasmids Encoding Interferon-γ Receptor/IgG1 or IL-4/IgG1 Chimeric Proteins Protects from Autoimmunity" *Journal of Gene Medicine* vol. 1, pp. 415-423 (1999).
Chen, et al., "A gene therapy approach for treating T-cell-mediated autoimmune diseases" *Blood* vol. 97, No. 4, pp. 886-894 (Feb. 2001).
Costa et al., "Targeting Rare Populations of Murine Antigen-Specific T Lymphocytes by Retroviral Transduction for Potential Application in Gene Therapy for Autoimmune Disease" *Journal of Immunology* vol. 164, pp. 3581-3590 (2000).

(Continued)

*Primary Examiner* — Doug Schultz
(74) *Attorney, Agent, or Firm* — Elaine T. Sale; Leigh W. Thorne

(57) ABSTRACT

A method is provided for treating or preventing an undesired immune response in a patient, comprising: administering to said patient, cells that transiently express, and/or that are transfected with mRNA encoding, one or more polypeptides selected from the group consisting of an IL-4 receptor agonist, an IFN-γ receptor antagonist, an IFN-α receptor antagonist, an IL-12 receptor antagonist, an IL-23 receptor antagonist, and a TNF antagonist. Preferably, the cells selectively accumulate in one or more secondary lymphoid tissues at or proximate to the site of the undesired immune response. Related compositions are provided. The methods and compositions are useful for the treatment or prevention of undesired immune responses including, but not limited to, transplant rejection, autoimmune disease, allergy and immune responses directed against therapeutic compositions.

9 Claims, 8 Drawing Sheets

(56) References Cited

OTHER PUBLICATIONS

Costa et al., "Adoptive Immunotherapy of Experimental Autoimmune Encephalomyelitis Via T Cell Delivery of the IL-12 p40 Subunit" *Journal of Immunology* Vo. 167, pp. 2379-2387 (2001).

Creusot et al., "Gene therapy for type 1 diabetes: a novel approach for targeted treatment of autoimmunity" *Journal of Clinical Investigation* Vo. 114, No. 7, pp. 892-894 (Oct. 2004).

Creusot et al., "Tissue-targeted therapy of autoimmune diabetes using dendritic cells transduced to express IL-4 in NOD mice" *Clin Immunol.* vol. 127, No. 2, pp. 176-187 (May 2008).

Creusot et al., "Lymphoid tissue-specific homing of bone marrow-derived dendritic cells" *Blood* vol. 113, No. 26, pp. 6638-6647 (2009)

Croxford et al., "Cytokine Gene Therapy in Experimental Allergic Encephalomyelitis by Injection of Plasmid DNA-Cationic Liposome Complex into the Central Nervous System" *Journal of Immunology* Vo. 160, pp. 5181-5187 (1998).

Feili-Hariri et al., "Immunotherapy of NOD Mice With Bone Marrow-Derived Dendritic Cells" *Diabetes* vol. 48, pp. 2300-2308 (Dec. 1999).

Feili-Hariri et al., "Dendritic Cell Immunotherapy for Autoimmune Diabetes" *Immunologic Research* vol. 36, No. 1-3, pp. 167-173 (2006).

Gallichan et al., "Pancreatic IL-4 Expression Results in Islet-Reactive Th2 Cells That Inhibit Diabetogenic Lymphocytes in the Nonobese Diabetic Mouse" *Journal of Immunology* vol. 163, pp. 1696-1703 (1999).

Guichelaar et al., "Autoantigen-Specific IL-10-Transduced T Cells Suppress Chronic Arthritis by Promoting the Endogenous Regulatory IL-10 Response" *Journal of Immunology* vol. 180, pp. 1373-1381 (2008).

Hayashi et al., "Induction of Th2-direted-immune responses by IL-4-transduced dendritic cells in mice" *Vaccine* vol. 18, pp. 3097-3105 (2000).

Healey et al., "In Vivo Activity and In Vitro Specificity of CD4+ Th1 and Th2 Cells Derived from the Spleens of Diabetic NOD Mice" *J. Clin. Invest.* vol. 95, pp. 2979-2985 (Jun. 1995).

Hogaboam et al., "Therapeutic Effects of Interleukin-4 Gene Transfer in Experimental Inflammatory Bowel Disease" *J. Clin. Invest.* vol. 100, No. 11, pp. 2766-2776 (Dec. 1997).

Kawamoto et al., "Suppression of Th1 cell activation and prevention of autoimmune diabetes in NOD mice by local expression of viral IL-10" *International Immunology* vol. 13, No. 5, pp. 685-694 (Feb. 2001).

Lee et al., "Prevention of Autoimmune Insulitis by Delivery of Interleukin-4 Plasmid Using a Soluble and Biodegradable Polymeric Carrier" *Pharmaceutical Research* vol. 19, No. 3, pp. 246-249 (Mar. 2002).

Morita et al., "Dendritic cells genetically engineered to express IL-4 inhibit murine collagen-induced arthritis" *J. Clin. Invest.* vol. 107, pp. 1275-1284 (2001).

Mueller et al., "Pancreatic Expression of Interleukin-4 Abrogates Insulitis and Autoimmune Diabetes in nonobese Diabetic (NOD) Mice" *J. Exp. Med.* vol. 184, pp. 1093-1099 (Sep. 1996).

Papaccio et al., "Prevention of Spontaneous Autoimmune Diabetes in NOD Mice by Transferring in Vitro Antigen-Pulsed Syngeneic Dendritic Cells" *Endocrinology* vol. 141, No. 4, pp. 1500-1505 (2000).

Piccirillo et al., "Immune Modulation by Plasmid DNA-mediated Cytokine Gene Transfer" *Current Pharmaceutical Design* vol. 9, pp. 83-94 (2003).

Pop et al., "The Type and Frequency of Immunoregulatory CD4+ T-Cells Govern the Efficacy of Antigen-Specific Immunotherapy in Nonobese Diabetic Mice" *Diabetes* vol. 56, pp. 1395-1402 (2007).

Rapoport et al., "Interleukin 4 Reverses T Cell Proliferative Unresponsiveness and Prevents the Onset of Diabetes in Nonobese Diabetic Mice" *J. Exp. Med.* vol. 178, pp. 87-99 (Jul. 1993).

Ricordi et al., "Clinical Islet Transplantation: Advances and Immunological Challenges" *Nature Reviews—Immunology* vol. 4, pp. 259-269 (Apr. 2004).

Kawamoto et al., Suppression of T(h)1 cell activation and prevention of autoimmune diabetes in NOD mice by local expression of viral IL-10. *Int. Immunol* vol. 13, No. 5, pp. 685-694 (May 2001).

Geurts et al., "Application of a disease-regulated promoter is a safer mode of local IL-4 gene therapy for arthritis," Gene Therapy, Dec. 2007, pp. 1632-1638, vol. 14, No. 23.

Van Tendeloo et al., "Highly Efficient Gene Delivery by mRNA Electroporation in Human Hematopoietic Cells: Superiority to Lipofection and Passive Pulsing of mRNA and to Electroporation of Plasmid CDNA for Tumor Antigen Loading of Dendritic Cells", Blood, Jul. 2001, pp. 49-56, vol. 98, No. 1.

Tarner et al., "Treatment of Autoimmune Disease by Adoptive Cellular Gene Therapy," Ann. NY Acad. Sci., Sep. 2003, pp. 512-519, vol. 998.

* cited by examiner

| TISSUE | IV INJECTION | IP INJECTION |
|---|---|---|
| SPLEEN | ++++ | +/- |
| PANCREATIC LN | +++ | ++++ |
| MESENTERIC LN | + | ++ |
| LUMBAR LN | - | ++ |
| INGUINAL LN | - | +/- |
| MEDIASTINAL LN | +++ | - |
| CERVICAL LN | - | - |
| THYMUS | - | - |
| PANCREAS | - | - |
| OMENTAL TISSUE | - | ++++ |
| LUNGS | (++++) | - |
| LIVER | (+++) | + |

*FIG. 1*

SEQUENCE LISTING

```
<160> NUMBER OF SEQ ID NOS: 6

<210> SEQ ID NO 1
<211> LENGTH: 3196
<212> TYPE: DNA
<213> ORGANISM: Artificial sequence
<220> FEATURE:
<223> OTHER INFORMATION: Synthetic nucleic acid
<220> FEATURE:
<221> NAME/KEY: promoter
<222> LOCATION: (2487)..(2506)
<223> OTHER INFORMATION: T7 promoter
<220> FEATURE:
<221> NAME/KEY: CDS
<222> LOCATION: (2551)..(2970 )
<223> OTHER INFORMATION: mIL4 coding sequence
<220> FEATURE:
<221> NAME/KEY: 3'UTR
<222> LOCATION: (2983)..(3121)
<223> OTHER INFORMATION: Rotavirus gene 6 3' UTR element
<220> FEATURE:
<221> NAME/KEY: misc_feature
```

<222> LOCATION: (3128)..(3191)
<223> OTHER INFORMATION: oligo T stretch

<400> SEQUENCE: 1

| | | | | | |
|---|---|---|---|---|---|
| cctgggggcg | cctgatgcgg | tattttctcc | ttacgcatct | gtgcggtatt | tcacaccgca | 60 |
| tatggtgcac | tctcagtaca | atctgctctg | atgccgcata | gttaagccag | ccccgacacc | 120 |
| cgccaacacc | cgctgacgcg | ccctgacggg | cttgtctgct | cccggcatcc | gcttacagac | 180 |
| aagctgtgac | cgtctccggg | agctgcatgt | gtcagaggtt | ttcaccgtca | tcaccgaaac | 240 |
| gcgcgagacg | aaagggcctc | gtgatacgcc | tatttttata | ggttaatgtc | atgataataa | 300 |
| tggtttctta | gacgtcaggt | ggcactttc | ggggaaatgt | gcgcggaacc | cctatttgtt | 360 |
| tatttttcta | aatacattca | aatatgtatc | cgctcatgag | acaataaccc | tgataaatgc | 420 |
| ttcaataata | ttgaaaaagg | aagagtatga | gtattcaaca | tttccgtgtc | gcccttattc | 480 |
| ccttttttgc | ggcattttgc | cttcctgttt | ttgctcaccc | agaaacgctg | gtgaaagtaa | 540 |
| aagatgctga | agatcagttg | ggtgcacgag | tgggttacat | cgaactggat | ctcaacagcg | 600 |
| gtaagatcct | tgagagtttt | cgccccgaag | aacgttttcc | aatgatgagc | acttttaaag | 660 |
| ttctgctatg | tggcgcggta | ttatcccgta | ttgacgccgg | gcaagagcaa | ctcggtcgcc | 720 |
| gcatacacta | ttctcagaat | gacttggttg | agtactcacc | agtcacagaa | aagcatctta | 780 |
| cggatggcat | gacagtaaga | gaattatgca | gtgctgccat | aaccatgagt | gataacactg | 840 |
| cggccaactt | acttctgaca | acgatcggag | gaccgaagga | gctaaccgct | tttttgcaca | 900 |
| acatggggga | tcatgtaact | cgccttgatc | gttgggaacc | ggagctgaat | gaagccatac | 960 |
| caaacgacga | gcgtgacacc | acgatgcctg | tagcaatggc | aacaacgttg | cgcaaactat | 1020 |
| taactggcga | actacttact | ctagcttccc | ggcaacaatt | aatagactgg | atggaggcgg | 1080 |
| ataaagttgc | aggaccactt | ctgcgctcgg | cccttccggc | tggctggttt | attgctgata | 1140 |
| aatctggagc | cggtgagcgt | gggtctcgcg | gtatcattgc | agcactgggg | ccagatggta | 1200 |
| agccctcccg | tatcgtagtt | atctacacga | cggggagtca | ggcaactatg | gatgaacgaa | 1260 |
| atagacagat | cgctgagata | ggtgcctcac | tgattaagca | ttggtaactg | tcagaccaag | 1320 |
| tttactcata | tatactttag | attgatttaa | aacttcattt | ttaatttaaa | aggatctagg | 1380 |
| tgaagatcct | ttttgataat | ctcatgacca | aaatccctta | acgtgagttt | tcgttccact | 1440 |
| gagcgtcaga | ccccgtagaa | aagatcaaag | gatcttcttg | agatcctttt | tttctgcgcg | 1500 |
| taatctgctg | cttgcaaaca | aaaaaaccac | cgctaccagc | ggtggtttgt | ttgccggatc | 1560 |
| aagagctacc | aactctttt | ccgaaggtaa | ctggcttcag | cagagcgcag | ataccaaata | 1620 |
| ctgttcttct | agtgtagccg | tagttaggcc | accacttcaa | gaactctgta | gcaccgccta | 1680 |
| catacctcgc | tctgctaatc | ctgttaccag | tggctgctgc | cagtggcgat | aagtcgtgtc | 1740 |
| ttaccgggtt | ggactcaaga | cgatagttac | cggataaggc | gcagcggtcg | ggctgaacgg | 1800 |
| ggggttcgtg | cacacagccc | agcttggagc | gaacgaccta | caccgaactg | agatacctac | 1860 |
| agcgtgagct | atgagaaagc | gccacgcttc | ccgaagggag | aaaggcggac | aggtatccgg | 1920 |
| taagcggcag | ggtcggaaca | ggagagcgca | cgagggagct | tccaggggga | aacgcctggt | 1980 |
| atctttatag | tcctgtcggg | tttcgccacc | tctgacttga | gcgtcgattt | ttgtgatgct | 2040 |
| cgtcaggggg | gcggagccta | tggaaaaacg | ccagcaacgc | ggccttttta | cggttcctgg | 2100 |
| ccttttgctg | gccttttgct | cacatgttct | ttcctgcgtt | atcccctgat | tctgtggata | 2160 |
| accgtattac | cgcctttgag | tgagctgata | ccgctcgccg | cagccgaacg | accgagcgca | 2220 |
| gcgagtcagt | gagcgaggaa | gcggaagagc | gcccaatacg | caaaccgcct | ctccccgcgc | 2280 |

-continued

```
gttggccgat tcattaatgc agctggcacg acaggtttcc cgactggaaa gcgggcagtg      2340
agcgcaacgc aattaatgtg agttagctca ctcattaggc accccaggct ttacacttta      2400
tgcttccggc tcgtatgttg tgtggaattg tgagcggata caatttcac acaggaaaca       2460 gctatgacca tgattacgcc aagctctaat acgactcact atagggagac aagcttcctg      2520
caggtcgact ctagaggatc ccgggaattc atg ggt ctc aac ccc cag cta gtt       2574
                                  Met Gly Leu Asn Pro Gln Leu Val
                                   1               5 gtc atc ctg ctc ttc ttt ctc gaa tgt acc agg agc cat atc cac gga        2622
Val Ile Leu Leu Phe Phe Leu Glu Cys Thr Arg Ser His Ile His Gly
         10                  15                  20 tgc gac aaa aat cac ttg aga gag atc atc gga ata ttg aac gag gtc        2670
Cys Asp Lys Asn His Leu Arg Glu Ile Ile Gly Ile Leu Asn Glu Val
 25                  30                  35                  40 aca gga gaa ggt acc cca tgc acg gag atg gat gtg cca aac gtc ctc        2718
Thr Gly Glu Gly Thr Pro Cys Thr Glu Met Asp Val Pro Asn Val Leu
                 45                  50                  55 aca gca acg aag aac acc aca gag agt gag ctc gtc tgt agg gct tcc        2766
Thr Ala Thr Lys Asn Thr Thr Glu Ser Glu Leu Val Cys Arg Ala Ser
             60                  65                  70 aag gtg ctt cgc ata ttt tat tta aaa cat ggg aaa act cca tgc ttg        2814
Lys Val Leu Arg Ile Phe Tyr Leu Lys His Gly Lys Thr Pro Cys Leu
         75                  80                  85 aag aag aac tct agt gtt ctc atg gag ctc cag aga ctc ttt cgg gct        2862
Lys Lys Asn Ser Ser Val Leu Met Glu Leu Gln Arg Leu Phe Arg Ala
 90                  95                 100 ttt cga tgc ctg gat tca tcg ata agc tgc acc atg aat gag tcc aag        2910
Phe Arg Cys Leu Asp Ser Ser Ile Ser Cys Thr Met Asn Glu Ser Lys
105                 110                 115                 120 tcc aca tca ctg aaa gac ttc ctg gaa agc cta aag agc atc atg caa        2958
Ser Thr Ser Leu Lys Asp Phe Leu Glu Ser Leu Lys Ser Ile Met Gln
                125                 130                 135 atg gat tac tcg tagtagctcg aggaccaagc taacaacttg gtatccaact            3010
Met Asp Tyr Ser
            140 ttggtgagta tgtagctata tcaagctgtt tgaactctgt aagtaaggat gcgtatacgc      3070 attcgctaca ctgagttaat cactctgatg gtatagtgag aggatgtgac cttaattaaa      3130 aaaaaaaaaa aaaaaaaaaa aaaaaaaaaa aaaaaaaaaa aaaaaaaaaa aaaaaaaaaa      3190 actagt                                                                 3196
```

<210> SEQ ID NO 2
<211> LENGTH: 140
<212> TYPE: PRT
<213> ORGANISM: Artificial sequence
<220> FEATURE:
<223> OTHER INFORMATION: Synthetic Construct

<400> SEQUENCE: 2

```
Met Gly Leu Asn Pro Gln Leu Val Val Ile Leu Leu Phe Phe Leu Glu
 1               5                  10                  15

Cys Thr Arg Ser His Ile His Gly Cys Asp Lys Asn His Leu Arg Glu
             20                  25                  30

Ile Ile Gly Ile Leu Asn Glu Val Thr Gly Glu Gly Thr Pro Cys Thr
         35                  40                  45

Glu Met Asp Val Pro Asn Val Leu Thr Ala Thr Lys Asn Thr Thr Glu
 50                  55                  60

Ser Glu Leu Val Cys Arg Ala Ser Lys Val Leu Arg Ile Phe Tyr Leu
```

```
                65                  70                  75                  80
Lys His Gly Lys Thr Pro Cys Leu Lys Lys Asn Ser Ser Val Leu Met
                        85                  90                  95

Glu Leu Gln Arg Leu Phe Arg Ala Phe Arg Cys Leu Asp Ser Ser Ile
            100                 105                 110

Ser Cys Thr Met Asn Glu Ser Lys Ser Thr Ser Leu Lys Asp Phe Leu
        115                 120                 125

Glu Ser Leu Lys Ser Ile Met Gln Met Asp Tyr Ser
    130                 135                 140

<210> SEQ ID NO 3
<211> LENGTH: 614
<212> TYPE: DNA
<213> ORGANISM: Homo sapiens
<220> FEATURE:
<221> NAME/KEY: CDS
<222> LOCATION: (64)..(522)
<223> OTHER INFORMATION: IL4 coding sequence
<220> FEATURE:
<221> NAME/KEY: sig_peptide
<222> LOCATION: (64)..(135)
<220> FEATURE:
<221> NAME/KEY: mat_peptide
<222> LOCATION: (136)..(522)

<400> SEQUENCE: 3
gatcgttagc ttctcctgat aaactaattg cctcacattg tcactgcaaa tcgacaccta      60 tta atg ggt ctc acc tcc caa ctg ctt ccc cct ctg ttc ttc ctg cta      108
    Met Gly Leu Thr Ser Gln Leu Leu Pro Pro Leu Phe Phe Leu Leu
        -20                 -15                 -10 gca tgt gcc ggc aac ttt gtc cac gga cac aag tgc gat atc acc tta      156
Ala Cys Ala Gly Asn Phe Val His Gly His Lys Cys Asp Ile Thr Leu
            -5                  -1  1                   5 cag gag atc atc aaa act ttg aac agc ctc aca gag cag aag act ctg      204
Gln Glu Ile Ile Lys Thr Leu Asn Ser Leu Thr Glu Gln Lys Thr Leu
                10                  15                  20 tgc acc gag ttg acc gta aca gac atc ttt gct gcc tcc aag aac aca      252
Cys Thr Glu Leu Thr Val Thr Asp Ile Phe Ala Ala Ser Lys Asn Thr
    25                  30                  35 act gag aag gaa acc ttc tgc agg gct gcg act gtg ctc cgg cag ttc      300
Thr Glu Lys Glu Thr Phe Cys Arg Ala Ala Thr Val Leu Arg Gln Phe
40                  45                  50                  55 tac agc cac cat gag aag gac act cgc tgc ctg ggt gcg act gca cag      348
Tyr Ser His His Glu Lys Asp Thr Arg Cys Leu Gly Ala Thr Ala Gln
                    60                  65                  70 cag ttc cac agg cac aag cag ctg atc cga ttc ctg aaa cgg ctc gac      396
Gln Phe His Arg His Lys Gln Leu Ile Arg Phe Leu Lys Arg Leu Asp
                75                  80                  85 agg aac ctc tgg ggc ctg gcg ggc ttg aat tcc tgt cct gtg aag gaa      444
Arg Asn Leu Trp Gly Leu Ala Gly Leu Asn Ser Cys Pro Val Lys Glu
            90                  95                  100 gcc aac cag agt acg ttg gaa aac ttc ttg gaa agg cta aag acg atc      492
Ala Asn Gln Ser Thr Leu Glu Asn Phe Leu Glu Arg Leu Lys Thr Ile
        105                 110                 115 atg aga gag aaa tat tca aag tgt tcg agc tgaatatttt aatttatgag      542
Met Arg Glu Lys Tyr Ser Lys Cys Ser Ser
120                 125 tttttgatag ctttattttt taagtattta tatatttata actcatcata aaataaagta      602
tatatagaat ct                                                         614

<210> SEQ ID NO 4
```

```
<211> LENGTH: 153
<212> TYPE: PRT
<213> ORGANISM: Homo sapiens

<400> SEQUENCE: 4

Met Gly Leu Thr Ser Gln Leu Leu Pro Pro Leu Phe Phe Leu Leu Ala
                -20                 -15                 -10

Cys Ala Gly Asn Phe Val His Gly His Lys Cys Asp Ile Thr Leu Gln
             -5              -1  1                  5

Glu Ile Ile Lys Thr Leu Asn Ser Leu Thr Glu Gln Lys Thr Leu Cys
 10                  15                  20

Thr Glu Leu Thr Val Thr Asp Ile Phe Ala Ala Ser Lys Asn Thr Thr
 25                  30                  35                  40

Glu Lys Glu Thr Phe Cys Arg Ala Ala Thr Val Leu Arg Gln Phe Tyr
                 45                  50                  55

Ser His His Glu Lys Asp Thr Arg Cys Leu Gly Ala Thr Ala Gln Gln
                 60                  65                  70

Phe His Arg His Lys Gln Leu Ile Arg Phe Leu Lys Arg Leu Asp Arg
                 75                  80                  85

Asn Leu Trp Gly Leu Ala Gly Leu Asn Ser Cys Pro Val Lys Glu Ala
 90                  95                 100

Asn Gln Ser Thr Leu Glu Asn Phe Leu Glu Arg Leu Lys Thr Ile Met
105                 110                 115                 120

Arg Glu Lys Tyr Ser Lys Cys Ser Ser
                125

<210> SEQ ID NO 5
<211> LENGTH: 146
<212> TYPE: PRT
<213> ORGANISM: Homo sapiens

<400> SEQUENCE: 5

Met His Pro Leu Leu Asn Pro Leu Leu Leu Ala Leu Gly Leu Met Ala
 1               5                  10                  15

Leu Leu Leu Thr Thr Val Ile Ala Leu Thr Cys Leu Gly Gly Phe Ala
                 20                  25                  30

Ser Pro Gly Pro Val Pro Pro Ser Thr Ala Leu Arg Glu Leu Ile Glu
                 35                  40                  45

Glu Leu Val Asn Ile Thr Gln Asn Gln Lys Ala Pro Leu Cys Asn Gly
                 50                  55                  60

Ser Met Val Trp Ser Ile Asn Leu Thr Ala Gly Met Tyr Cys Ala Ala
 65                  70                  75                  80

Leu Glu Ser Leu Ile Asn Val Ser Gly Cys Ser Ala Ile Glu Lys Thr
                 85                  90                  95

Gln Arg Met Leu Ser Gly Phe Cys Pro His Lys Val Ser Ala Gly Gln
                100                 105                 110

Phe Ser Ser Leu His Val Arg Asp Thr Lys Ile Glu Val Ala Gln Phe
                115                 120                 125

Val Lys Asp Leu Leu Leu His Leu Lys Lys Leu Phe Arg Glu Gly Gln
                130                 135                 140

Phe Asn
145

<210> SEQ ID NO 6
<211> LENGTH: 328
<212> TYPE: PRT
<213> ORGANISM: Homo sapiens
```

```
<400> SEQUENCE: 6

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325
```

TRANSIENT EXPRESSION OF IMMUNOMODULATORY POLYPEPTIDES FOR THE PREVENTION AND TREATMENT OF AUTOIMMUNE DISEASE, ALLERGY AND TRANSPLANT REJECTION

CROSS-REFERENCE TO RELATED APPLICATIONS

This application is a 35 U.S.C. §371 national stage application of International Patent Application PCT/US2009/001232 (published as WO 2009/108341), filed Feb. 27, 2009, which claimed priority of under 35 U.S.C. §119 of U.S. Provisional Application 61/067,459, filed Feb. 28, 2008.

STATEMENT REGARDING FEDERALLY SPONSORED RESEARCH

The research leading to this invention was supported in part by NIH grant 5P01 AI036535. Accordingly, the U.S. government may have certain rights in the invention.

FIELD OF THE INVENTION

The present invention relates to improved methods and compositions for cell therapy that are useful in the prevention and treatment of unwanted immune responses, including, but not limited to autoimmune disease, allergy, transplant rejection.

BACKGROUND OF THE INVENTION

A common feature in a number of autoimmune diseases and inflammatory conditions is the involvement of pro-inflammatory $CD4^+$ T cells. These T cells are responsible for the release of inflammatory Th1 type cytokines. Cytokines secreted by $CD4^+$ Th1 cells include IL-2, IFN-$\gamma$, TNF-$\alpha$ and IL-12. These pro-inflammatory cytokines stimulate the immune response and can result in the destruction of autologous tissue. Th2 cytokines are associated with suppression of T cell response, and include IL-10, IL-4 and TGF-$\beta$. Th2 cytokines have been used to suppress immune responses and to treat or prevent autoimmune diseases, such as type 1 diabetes and multiple sclerosis.

Type 1 diabetes (T1D, a.k.a. insulin dependent diabetes mellitus (IDDM)) is caused by T cell-mediated autoimmune destruction of insulin-producing $\beta$ cells in the pancreatic islets. Analysis of the immune response to $\beta$-cell antigens has shown that both CD4 and CD8 T-cells contribute to $\beta$-cell deletion, through mechanisms dependent on pro-inflammatory cytokines such as IL-12 and IFN-$\gamma$ that support a typical 'Th1' response. The non-obese diabetic (NOD) mouse is a well-recognized model for human IDDM. Female NOD mice develop spontaneous diabetes from approximately 20-30 weeks of age, following a pre-diabetic phase consisting of non-pathogenic autoantibody production, and peri-islet mononuclear cell infiltration, which develops at around 10-12 weeks of age. At 30 weeks of age, more than 80% of female mice have developed overt diabetes (hyperglycemia).

The ability to identify individuals at risk for IDDM, through detection of anti-$\beta$-cell autoantibodies prior to the onset of overt clinical disease, offers the potential to introduce immunotherapies that may subvert the development of a cell mediated response, resulting in a lack of progression to overt clinical symptoms. The classification of IDDM as a 'Th1' cell mediated response has lead to the development of immunotherapies that support the induction of counter regulatory networks dependent on the induction of 'Th2' immunity to $\beta$-cell antigens. As mentioned above, Th1 responses are dependent on the secretion of IL-12 from antigen presenting cells, and IFN-$\gamma$ from effector T-cells. IL-4 is a natural regulator of the Th1 compartment, and several studies employing systemic delivery of IL-4 have shown that this approach can prevent the onset of clinically overt diabetes in the NOD mouse model.

Multiple intraperitoneal (i.p.) injections of IL-4, when initiated at an early age, have been shown to prevent IDDM in NOD mouse models by producing a suppressive response in Th2 type T cells. For example, Rapaport et al. (J Exp Med (1993) 178:87-89) disclose that i.p. administration of recombinant IL-4 (twice weekly for 14 weeks) to prediabetic NOD mice beginning at 6 weeks of age reduced the incidence of IDDM to less than 10% compared to greater than 75% in control animals. Cameron et al. (J Immunol (1997) 159:4686-4692) confirmed this study and disclose that i.p. administration of recombinant IL-4 beginning at an earlier age (3 times a week for 10 weeks beginning at 2 weeks of age) improved protection.

As an alternative to injection of recombinant IL-4, gene therapy vectors have been employed, using both naked DNA and viral vector approaches (Chang and Prud'homme (J Gene Med (1999) 1:415-423) and Cameron et al. (2000 Human Gene Therapy 11:1647-1656)). Chang et al. administered a naked DNA plasmid encoding an IL-4/IgG1 chimeric protein with IL-4 activity by intramuscular injection to 3 or 6 week old NOD mice every 21 days for five administrations. Prolonged expression of the IL-4 fusion protein was detectable in muscle at days 7 and 21. The best protection against diabetes was obtained by injecting five doses of DNA at three-week intervals. Chang and Prud'homme concluded that delivery of constant, but low, cytokine levels over a relatively long period would be advantageous.

Cameron et al. compared the efficacy of two IL-4 DNA vectors, with and without an EBV origin for episomal replication, for the prevention of diabetes in NOD mice. Three biolistic epidermal inoculations of NOD mice (at 3, 5 and 7 weeks of age) with either DNA vector resulted in a reduction of insulitis and diabetes. Production of IL-4 (40-50 pg/ml) by the vector lacking an episomal origin of replication was observed in sera of treated NOD mice, but was not detectable at time points later than 3 days post inoculation. In contrast, the serum levels of mIL-4 produced by the vector containing the EBV origin of replication were higher (50-100 pg/ml) and were detectable at 12 days post-inoculation. At 30 weeks of age, 45% of mice treated with the non-replicating IL-4 vector, and 20% of the mice treated with the episomally maintained vector were diabetic, as compared to 90% of control mice. Cameron et al. observed that due to the short half life of IL-4 in vivo, multiple injections of this cytokine are required to protect NOD mice from IDDM (i.e., thrice weekly for 8-10 weeks). They concluded, "Cytokine immunotherapy with the intent to induce immune deviation is most effective in preventing the pathogenesis of T1D when initiated at an early age and maintained at low doses continuously during the prophylactic period."

Cameron et al. (Gene Therapy (2000) 7:1840-1846) treated NOD mice with two i.p. injections of recombinant replication deficient adenovirus type 5 vector expressing murine IL-4 (Ad5mIL-4) beginning at two weeks of age. This treatment delayed and reduced the incidence of diabetes from 80% in controls to 20% in Ad5mIL-4 treated mice. In Ad5mIL-4 treated mice, the onset of diabetes was delayed until 28 weeks of age, while in control mice, diabetes was observed as early as 14 weeks of age. IL-4 (1-2 ng/ml) was detectable in the serum of treated NOD mice for up to 3 days following each injection at 2 and 5 weeks of age, yet was undetectable after a third injection at 7 weeks. However, a single injection at 2 weeks of age did not reduce the incidence of IDDM in NOD mice, but resulted in a 10-week delay in onset as compared to controls. Interestingly, delaying administration of the gene therapy vector until mice were 5 weeks of age did not reduce diabetes incidence in later life.

Lee et al. (Pharmaceutical Res (2002) 19:246-249) administered an IL-4 expression plasmid complexed with a biodegradable carrier by a single i.v. injection to 4-week-old NOD mice. Exogenous IL-4 expression was detectable in the liver five days post injection and the severity of insulitis was reduced at 10 weeks of age.

Mueller et al. (JEM (1996) 184:1093) demonstrated that transgenic NOD mice expressing IL-4 in their pancreatic β cells under the control of the constitutive human insulin promoter are completely protected from insulitis and diabetes.

Feili-Hariri et al. (Diabetes (1999) 48:2300-2308) disclose that bone marrow derived dendritic cells (DCs) prepared in GM-CSF and IL-4, and adoptively transferred to 5-week-old prediabetic NOD mice by i.v. injection in the form of three doses, one week apart, could reduce diabetes incidence from 90% in controls to 20% in the treated cohort at 30 weeks. After i.v. injection, DCs migrated to the spleen, and to a lesser degree to the exocrine tissue of the pancreas, and induced regulatory $T_H2$ cells. This study concluded that DCs prepared in IL-4 may be able to alter the balance between Th1 and Th2 immunity in treated mice. To further examine this hypothesis, a later study (Feili-Hariri et al., Human Gene Therapy (2003) 14:13-23) utilized DCs transduced with adenoviral vectors expressing IL-4 (Ad/IL-4). The DCs migrated to the pancreatic lymph nodes within 24 hours of i.v. administration to NOD mice, but were not detectable after 72 hours. Treatment was most effective when administered to NOD mice at 5 and 8 weeks of age (20-25% of mice treated at 5 weeks with one or two injections of DCs transduced with Ad/IL-4 developed diabetes compared to 70-100% of control mice treated with PBS). However, when treatment was initiated in older prediabetic NOD mice (15 weeks of age), a few mice showed delay in onset, but no significant difference in diabetes incidence was observed between treated and PBS control groups.

U.S. Pat. No. 7,378,089 discloses administering dendritic cells and T cells genetically modified to contain an expression cassette encoding a suppressive agent, such as IL-4, for the treatment of autoimmune diseases, including diabetes.

IL-4 has been used to treat animal models of autoimmune diseases other than diabetes. For example, Picarillo and Prud'homme (Hum Gene Ther (1999) 10:1915-1922) disclose that intramuscular injection of a naked plasmid DNA expressing an IL-4/IgG1 chimeric protein protects mice from myelin basic protein-induced experimental allergic encephalomyelitis (EAE), a mouse model for multiple sclerosis. Bessis et al. (J Gene Med (2002) 3:300-307) disclose systemic injection of immortalized fibroblasts transfected with a plasmid encoding IL-4 results in clinical and histological improvement of joint inflammation and destruction in the mouse model of collagen-induced arthritis (CIA). Hogaboam et al. (J Clin Invest (1997) 100:2766-2776) disclose the use of adenoviral-based gene transfer of IL-4 for treatment in an experimental model of inflammatory bowel disease.

Gene therapy approaches using cytokines other than IL-4 have been used in a number of animal models of autoimmune diseases. For example, expression of TGF-β1, IL-10 or galectin-1 is protective in mouse models of diabetes (King et al. (1998) Immunity 8:601-613; Kawamoto et al. Int Immunol (2001) 13:685-695; Perone et al. (2006) J Immunol 117: 5278-5289). Costa et al. (J Immunol (2001) 167:2379-2387) disclose the use of myelin basic protein-specific T cells containing a retroviral vector expressing IL-12 p40 for the treatment of EAE, a mouse model for multiple sclerosis.

Guichelaar et al. (J Immunol (2008) 180:1373-1381) disclose cartilage proteoglycan-specific CD4+ T cells transduced with IL-10 for the treatment of proteoglycan-induced arthritis, a mouse model of arthritis. Smith et al. (Gene Ther. (2003) 10:1248-57) disclose the prevention of collagen-induced arthritis in mice by administration of a collagen reactive T-cell hybridoma expressing an anti-TNF single-chain antibody. Transgene expression was detected in the paws but not the spleen of treated animals for up to 55 days postinjection.

U.S. Pat. No. 6,670,186 proposes loading antigen presenting cells with RNA encoding an immunomodulator (i.e., IL-1, IL-2, IL-3, IL-4, IL-5, IL-6, IL-7, IL-8, IL-9, IL-10, IL-11, IL-12, or IL-15, or GM-CSF) together with RNA encoding a tumor-derived or pathogen antigen. According to the '186 patent, the RNA-encoded immunomodulator is intended to enhance the immune response.

The immunosuppressive therapies discussed above involve sustained expression or repeated delivery of immunosuppressive cytokines or cytokine expression vectors. However, systemic or prolonged delivery of immunosuppressive cytokines can lead to toxicity, increased risk of infections and malignancies. Accordingly, there is a long-felt need in the art for effective, non-toxic therapies to prevent or treat autoimmune diseases, allergy and transplant rejection.

SUMMARY OF THE INVENTION

Previous approaches to prevention or therapy of autoimmune diseases, allergy and transplant rejection have emphasized the need for sustained delivery of immunosuppressive compounds. For example, the data discussed above using recombinant IL-4, or naked DNA vectors and adenoviral constructs encoding the cytokine, suggests that long term maintenance of IL-4 expression is required to prevent progression to overt diabetes, and is most effective when therapy was initiated prior to the pre-diabetic phase (2-8 weeks of age). Surprisingly, the inventors have discovered that cell therapies utilizing cells that only briefly express an immunomodulatory polypeptide are capable of delaying the onset and reducing the incidence of a dysfunction or an undesired immune response. This brief expression can be accomplished via transient expression of an immunomodulatory polypeptide encoded by DNA, or by transfection of a cell with mRNA encoding the immunomodulatory polypeptide.

Accordingly, a method is provided for treating or preventing an undesired immune response in a patient, comprising: administering to said patient, cells transfected with mRNA encoding one or more immunosuppressive polypeptides selected from the group consisting of an IL-4 receptor agonist, an IL-12 receptor antagonist, an IL-23 receptor antagonist, an interferon gamma (IFN-γ) receptor antagonist, an interferon alpha (IFN-α) receptor antagonist, and a TNF-α receptor antagonist.

In some embodiments, the cells are co-transfected with mRNA encoding one or more of the above immunomodulatory polypeptides together with mRNA encoding one or more additional immunomodulators selected from the group consisting of anti-CD40 ligand (CD40L) antibody, Flt3 ligand (Flt3L), IL-2, OX40L, CD200, TGF-β, programmed cell death ligand 1 (PDL1), programmed cell death ligand 2

(PDL2), soluble CD83, IL-10, IL-19, IL-33, galectin-1, CTLA-4, CD103, anti-IL-17 antibody, and indoleamine 2,3-dioxygenase (IDO).

In yet another aspect, an isolated cell transfected with mRNA is provided, wherein at least 5% of said transfected mRNA encodes a polypeptide selected from the group consisting of an IL-4 receptor agonist, an IL-12 receptor antagonist, an IL-23 receptor antagonist, an IFN-γ receptor antagonist, an IFN-α receptor antagonist, and a TNF receptor antagonist, wherein said cells are not transfected with RNA encoding tumor or pathogen antigens and wherein said cell is selected from the group consisting of B cells, T cells, macrophages, fibroblasts, dendritic cells and artificial antigen-presenting cells.

In still another aspect, a method is provided for treating or preventing an undesired immune response in a patient, comprising: administering to said patient, cells which transiently express one or more immunosuppressive polypeptides selected from the group consisting of an IL-4 receptor agonist, an IL-12 receptor antagonist, an IL-23 receptor antagonist, an IFN-γ receptor antagonist, an IFN-α receptor antagonist, and a TNF-α receptor antagonist.

Preferably, the cells used in the methods and compositions of the invention are selected from the group consisting of B cells, B cell hybridomas, T cells, T cell hybridomas, macrophages, fibroblasts, dendritic cells and artificial antigen-presenting cells. Most preferably, the cells are dendritic cells. In a preferred embodiment, following administration, the cells selectively accumulate in a secondary lymphoid tissue in the proximate vicinity of the undesired immune response.

In a further aspect, an isolated cell is provided, wherein the cell is transfected or transduced with an expression cassette comprising a nucleic acid encoding one or more polypeptides selected from the group consisting of an IL-4 receptor agonist, an IL-12 receptor antagonist, an IL-23 receptor antagonist, an IFN-γ receptor antagonist, an IFN-α receptor antagonist, and a TNF receptor antagonist, wherein said nucleic acid is operatively linked to a heterologous inducible promoter, wherein said cell is selected from the group consisting of B cells, T cells, macrophages, fibroblasts, dendritic cells and artificial antigen-presenting cells.

The compositions and methods disclosed herein are useful for therapeutic purposes and thus are intended to prevent, cure, or alleviate at least one symptom of a disease or disorder caused by the dysfunction or undesired function of an immune response, such as, but not limited to transplant rejection, allergy, immune responses directed against therapeutic compositions, (e.g., gene therapy vectors, stem cell therapy, protein replacement therapy, etc.) and autoimmune diseases, including, but not limited to insulin dependent diabetes mellitus, multiple sclerosis, rheumatoid arthritis, psoriasis, systemic lupus erythematosus, ulcerative colitis, chronic obstructive pulmonary disease and asthma.

In preferred embodiments, the autoimmune disease is insulin dependent diabetes mellitus. In one embodiment, overt diabetes is prevented by initiating treatment when anti-islet antibodies are detected in a patient. In particular, such an anti-islet antibody may be specific for glutamate decarboxylase (GAD), insulinoma associated peptide-2 (IA-2) or insulin.

BRIEF DESCRIPTION OF THE FIGURES

FIG. 1 shows typical biodistributions of murine bone-marrow derived dendritic cells following i.p. or i.v. administration. (+++)=transient expression in lungs and liver relative to spleen and lymph nodes.

FIG. 6 shows the level of IL-4 secretion over 24 hours from mouse bone marrow derived DCs transduced with a lentiviral IL-4 expression vector (ltDC/IL-4) versus DCs electroporated with IL-4 RNA (eDC/IL-4).

DETAILED DESCRIPTION OF THE EMBODIMENTS

Figure 2:
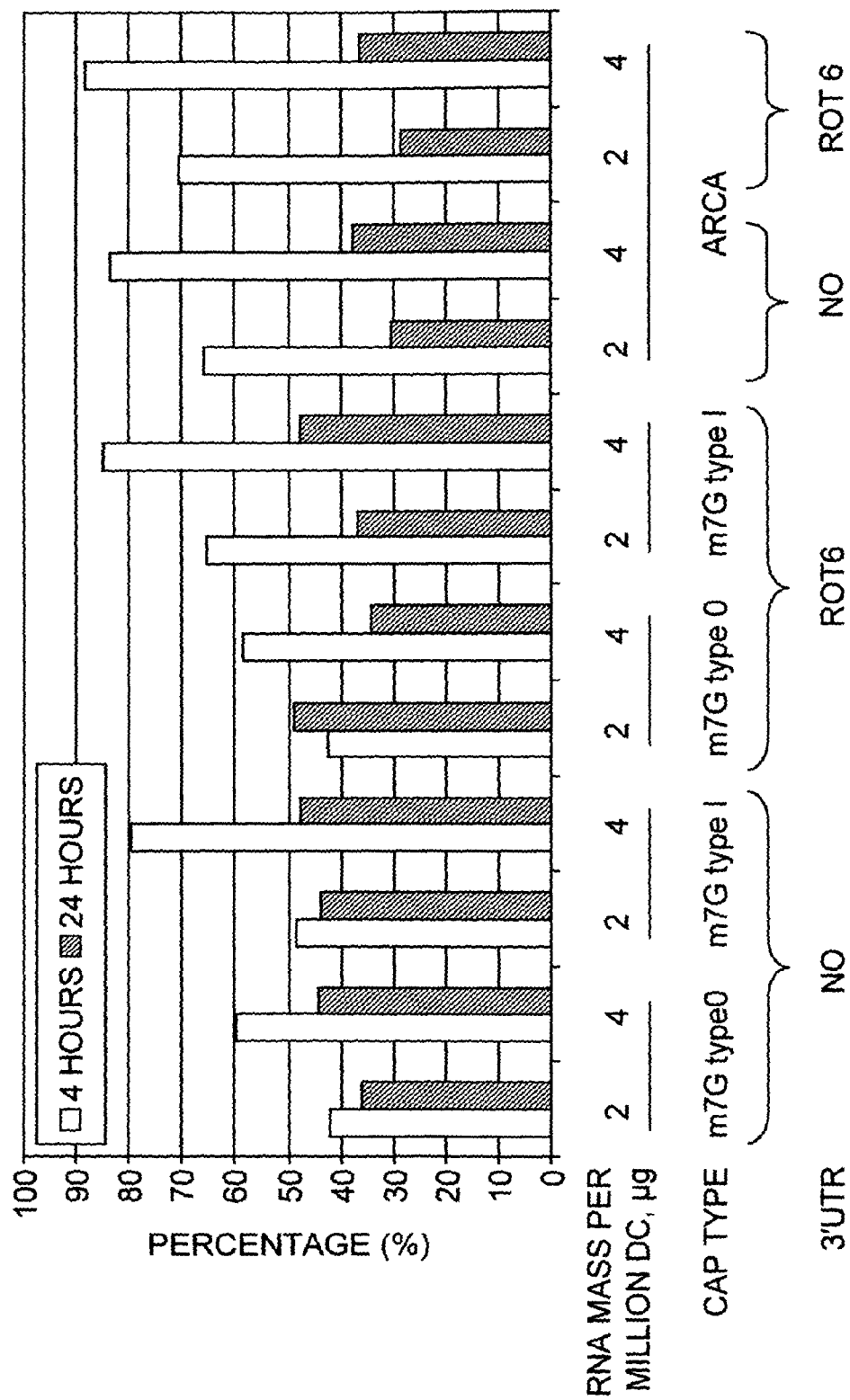
FIG. 2 shows the effect of mRNA modifications, such as various types of 5' capping (e.g., ARCA, m7G type 1 and m7G type 2) and the presence or absence of the rotavirus gene 6 3'UTR on the percentage of mRNA transfected human immature dendritic cells expressing murine IL-4 at 4 and 24 hrs post transfection.

Previous attempts to treat autoimmune disease using adoptive cell therapy were directed toward sustained expression of immunosuppressive proteins, such as IL-4, IL-10 and IL-12 p40, which are involved in the suppression of Th1 effects and the inducement of Th2 effects. Researchers in this field of endeavor have emphasized that prolonged expression (typically 3-12 days) or repeated administration of the immunosuppressive protein is necessary to effectively treat autoimmune diseases.

Surprisingly, the present inventors have discovered that only brief expression of an immunomodulatory polypeptide by cells that localize in secondary lymphoid tissue in the proximate vicinity of an undesired immune response is sufficient to reduce or prevent undesired immune responses, such as autoimmune diseases, allergy and transplant rejection, or to induce tolerance to a therapeutic compound, such as a therapeutic protein, a gene therapy vector, stem cells, etc.

This brief expression can be accomplished via transient expression from an expression cassette encoding one or more immunomodulatory polypeptides, or preferably by transfection of cells with mRNA encoding one or more immunomodulatory polypeptides.

There are a number of advantages to the mRNA approach as compared to approaches using viral vectors, expression cassettes, and/or DNA. First, there is no danger of disruption of the genome of the host cell by insertional mutagenesis. Second, delivery of mRNA does not require the use of viral vectors, which are commonly used for gene delivery. An immune response to viral antigen expressed by cells transduced with viral vectors often results in elimination of the transferred cell and a reduction in therapeutic effect. Finally, the mRNA approach poses fewer regulatory hurdles than gene therapy approaches.

Accordingly, a method is provided for treating or preventing an undesired immune response in a patient, comprising: administering to said patient, cells transfected with mRNA encoding a polypeptide selected from the group consisting of an IL-4 receptor agonist, an IL-12 receptor antagonist, an IL-23 receptor antagonist, an IFNγ receptor antagonist, an IFNα receptor antagonist and a TNFα receptor antagonist. Preferably, the mRNA encodes IL-4, most preferably human IL-4.

In another embodiment, an isolated cell transfected with mRNA is provided, wherein at least 5% of said mRNA encodes a polypeptide selected from the group consisting of an IL-4 receptor agonist, an IL-12 receptor antagonist, an IL-23 receptor antagonist, an IFNγ receptor antagonist, an IFNα receptor antagonist, and a TNFα receptor antagonist, wherein said cells are not transfected with RNA encoding tumor or pathogen antigens and wherein said cell is selected from a B cell, a B cell hybridoma, a T cell, a T cell hybridoma, a macrophage, a fibroblast, an artificial antigen presenting cell or a dendritic cell.

The polypeptide sequences of IL-4 receptor agonists, IL-12 receptor antagonists, IL-23 receptor antagonists, IFNγ receptor antagonists, IFNα receptor antagonists, and TNF receptor antagonists are known in the art, as well as nucleic acids encoding such polypeptides. Using routine techniques, the known sequence information can be used to isolate additional sequences encoding the foregoing polypeptides.

As used herein, a polypeptide antagonist of a receptor is a polypeptide which interferes with the binding of the native ligand to a receptor and/or which prevents activation of the receptor. As non-limiting examples, the antagonist could bind the receptor without activating it and prevent binding and activation by the native ligand, or the antagonist could bind the native ligand and prevent binding of the ligand to the receptor. Non-limiting examples of receptor antagonists include antibodies that bind to the ligand of the receptor and thereby prevent productive receptor ligand interactions, and antibodies that bind to the receptor without activating it and block ligand binding.

Preferably, the immunomodulatory polypeptide is an interleukin 4 (IL-4) receptor agonist. IL-4 receptor agonists are known in the art, and include IL-4 and IL-13 and variants thereof that have one or more of the biological activities of said polypeptides. Variant polypeptides may differ from native polypeptides by the deletion, insertion or substitution of one or more amino acids. Conservative substitutions, wherein the substituted amino acid is of a similar nature (e.g., charge, size, polarity and/or hydrophobicity) to the one present in the naturally occurring protein are preferred. DNA and RNA sequences encoding any given polypeptide sequence can easily be determined by one of skill in the art.

Additional IL-4 receptor agonists include agonistic IL-4 receptor antibodies and any other polypeptides that bind and activate IL-4 receptors. Preferably, the IL-4 receptor agonist is IL-4, most preferably, it is human IL-4. IL-4 polypeptide sequences are known in the art, as are methods for isolating novel IL-4 sequences and assaying for IL-4 activity. Numerous IL-4 protein sequences are disclosed in GenBank. Examples of murine IL-4 polypeptides include, but are not limited to GenBank Accession numbers NP_067258, BAD83771 and IL-4 sequence shown in SEQ ID NO:2.

Examples of human IL-4 polypeptides include, but are not limited to, GenBank Accession numbers AAH70123, AAH67514, CAA57444, and the human IL-4 sequence disclosed in Yokota et al. (PNAS (1986) 83:5894-5898), which is SEQ ID NO:4. Amino acid residues 1-24 of SEQ ID NO:4 correspond to the signal sequence of human IL-4, and amino acid residues 25-153 of SEQ ID NO:4 correspond to the mature human IL-4 protein. A corresponding human IL-4 mRNA is shown in SEQ ID NO:3. In preferred embodiments, the IL-4 polypeptide used in the methods of the invention has at least 80% sequence identity with the amino sequence of GenBank Accession number AH70123, AAH67514 or CAA57444, or the human IL-4 sequence disclosed in Yokota et al. (PNAS (1986) 83:5894-5898). Most preferably, the IL-4 polypeptide has at least 85%, 90%, 95%, 96%, 97%, 98% or 99-100% sequence identity with the sequence of GenBank Accession number AAH70123, AAH67514 or CAA57444, or the human IL-4 sequence disclosed in Yokota et al. (PNAS (1986) 83:5894-5898).

In one embodiment, the IL-4 receptor agonist is an IL-13 polypeptide. IL-13 polypeptide sequences are known in the art, as are methods for isolating novel IL-13 sequences. The sequence of a murine IL-13 is disclosed in GenBank Accession number NP_032381. Examples of human IL-13 polypeptides include, but are not limited to, GenBank Accession numbers AAH96141; AAH96139; AAH96140; AAH96138 and SEQ ID NO:5. Preferred IL-13 polypeptides useful in the methods of the invention have a sequence with at least 80% identity, more preferably at least 85%, 90%, 95%, 96%, 97%, 98% or 99-100% sequence identity with a polypeptide having GenBank accession number NP_032381; AAH96141; AAH96139; AAH96140; AAH96138; and/or SEQ ID NO:5.

Polypeptide antagonists of IL-12 receptor or IL-23 receptor include, but are not limited to polypeptides that bind, but do not activate IL-12 receptor or IL-23 receptor, such as the IL-12 p40 subunit, which is shared by IL-12 and IL-23. In addition, antagonists include any polypeptides that interfere with IL-12/IL-12 receptor or IL-23/IL-23 receptor interactions, such as soluble IL-12 receptor or soluble IL-23 receptor, soluble IL-12 receptor-Ig fusion proteins, soluble IL-23 receptor-Ig fusion proteins, and antibodies to IL-12 or IL-23, or IL-12 receptor or IL-23 receptor. Such antibodies, IL-12 p40 subunit sequences, soluble IL-12 receptor and soluble IL-23 receptor sequences are known in the art. An example of a human IL-12 p40 sequence is disclosed in GenBank accession number AAD56386 and SEQ ID NO:6. An example of a murine IL-12 p40 sequence is disclosed in GenBank accession number AAA39296. Preferred IL-12 p40 polypeptides useful in the methods of the invention have a sequence with at least 80% identity, more preferably at least 85%, 90%, 95%, 96%, 97%, 98% or 99-100% sequence identity with a polypeptide having GenBank accession number AAD56386 or AAA39296.

Polypeptide antagonists of TNFα receptors are known in the art, and include, but are not limited to anti-TNFα antibodies, anti-TNFα receptor antibodies, polypeptides that bind but do not activate TNFα receptor, any polypeptides that interfere with TNFα/TNFα receptor interactions, such as soluble TNFα receptor, and Ig fusions thereof. In a preferred embodiment, the anti-TNFα antibody is a single chain construct of an anti-TNFα antibody (scFv) (See, for example, Smith et al. (Gene Ther (2003) 10:1248-57.)

Polypeptide antagonists of IFNα receptors are known in the art, and include, but are not limited to anti-IFNα antibodies (see, for example U.S. Pat. No. 7,087,726 and U.S. Patent Publication 20080160030), anti-IFNα receptor antibodies, polypeptides that bind but do not activate IFNα receptor, any polypeptides that interfere with IFNα/IFNα receptor interactions, such as soluble IFNα receptor, and Ig fusions thereof.

Polypeptide antagonists of IFNγ receptors are known in the art, and include, but are not limited to anti-IFNγ antibodies (see, for example, Van der Meide et al. (1985) J Immunol Methods 79(2):293-305), anti-IFNα receptor antibodies, polypeptides that bind but do not activate IFNγ receptor, any polypeptides that interfere with IFNγ/IFNγ receptor interactions, such as soluble IFNγ receptor, and Ig fusions thereof. See, for example, U.S. Patent Publication 20070020283 and U.S. Pat. No. 5,612,195.

Table 1 lists co-modulatory polypeptides that are relevant to type 1 diabetes, multiple sclerosis, psoriasis, SLE, asthma and transplant rejection. As used in the table, "anti-XXX" (e.g., anti-TNFα, etc.) refers to an immunomodulatory polypeptide that antagonizes either the cytokine (e.g., TNFα, etc.) or its receptor. The neutralizing polypeptides include, but are not limited to antibodies that bind a receptor or its ligand, soluble receptor polypeptides, other polypeptides that interfere with cytokine/receptor interactions, and the like. mRNA encoding one or more of such co-modulatory polypeptides can be co-transfected with mRNA encoding one or more immunomodulators selected from the group consisting of IL-4 receptor agonists, IL-12 receptor antagonists, IL-23 receptor antagonists, IFNγ receptor antagonists, IFNα receptor antagonists, and TNF receptor antagonists.

ing of an IL-4 receptor agonist, an IL-12 receptor antagonist, an IL-23 receptor antagonist, an IFNγ receptor antagonist, an IFNα receptor antagonist, and a TNFα receptor antagonist; together with mRNA encoding one or more additional immunomodulators selected from the group consisting of anti-CD40 ligand (CD40L) antibody, Flt3 ligand (Flt3L), IL-2, OX40L, CD200, TGF-β, programmed cell death ligand 1 (PDL1), programmed cell death ligand 2 (PDL2), soluble CD83, OX40L, IL-2, IL-10, IL-12 p40, anti-IL-12 antibody, IL-19, IL-33, galectin-1, CTLA-4, CD103, anti-IL-17 antibody, and indoleamine 2,3-dioxygenase (IDO). Amino acid and nucleic acid sequences of homing polypeptides and these immunomodulators are known, and additional sequences can be isolated by one of ordinary skill in the art.

The term "soluble CD83" or "sCD83" as used herein refers to a polypeptide that comprises at least a portion of the extracellular domain of a member of the CD83 family of proteins. Preferred soluble CD83 polypeptides and nucleic acids are disclosed in U.S. patent publication 2007/0167607. In one embodiment, the amino acid sequence of human sCD83 consists of amino acid residues 20-144 or 20-145 of GenBank Accession No. Q01151. In some embodiments, CD83 may be a monomer; in such embodiments, one or more of the native cysteine residues of CD83 may be replaced by another amino acid residue, e.g., a small and/or polar amino acid residue. In some embodiments, the term "soluble CD83" or "sCD83" encompasses fusion proteins of at least a portion of the extracellular domain of CD83 and functional fragments and derivatives (see, e.g., WO 2004/046182).

Methods for making mRNA and transfecting such cells with mRNA are known to those of skill in the art. Typically, the RNA will be generated by in vitro transcription from a plasmid template. In vitro transcription systems using T7 or SP6 promoters operatively linked to a sequence of interest are well known in the art. The length of expression of the immu-

TABLE 1

| Disease Indication | Treatment | Mechanism of Action | Additional co-modulators |
| --- | --- | --- | --- |
| Type 1 Diabetes | Antagonism of cell mediated immunity by expression of: IL-4, IL-13, anti-TNF, anti-IL-12, and/or anti-IL-23 | Suppression of pro-inflammatory T cell priming; Generalized immunosuppression | IDO, sCD83, TGF-β, IL-19, IL-33, PDL-1, PDL-2, anti-IL-17, anti-CD40L, and/or CD103 |
| Multiple Sclerosis | Antagonism of cell mediated immunity by expression of: IL-4, IL-13, anti-TNF, anti-IL-12, anti-IL23, and/or anti-CD40L | Suppression of pro-inflammatory T cell priming; Generalized immunosuppression | IDO, sCD83, TGF-β, IL-19, IL-33, IL-10, PDL1, PDL2, anti-IL17, and/or anti-IFNγ |
| Psoriasis | Antagonism of cell mediated immunity by expression of: IL-4, IL-13, anti-TNF, anti-IL-12, anti-IL23, and/or anti-IFNα | Suppression of pro-inflammatory T cell priming; Generalized immunosuppression | IDO, sCD83, TGF-β, anti-IL-19, IL-33, IL-10, PDL1, PDL2, anti-IL-17, anti-IFNγ, and/or anti-CD40L |
| SLE | Antagonism of humoral immunity by expression of: anti-IL4, anti-IL-13, IL-12, anti-IL-10, and/or anti-IFNα | Immune deviation - split tolerance; Generalized immunosuppression | IDO, sCD83, TGF-β, IL-19, anti-IL-33, PDL-1, and/or PDL-2 |
| Asthma | Antagonism of cell mediated immunity by expression of: anti-IL-4, anti-IL13, IL-12, anti-IL-10, and/or IFNγ | Immune deviation - split tolerance; Generalized immunosuppression | IDO, sCD83, TGF-b, IL-19, anti-IL-33, PDL-1; and/or PDL-2 |
| Transplant Rejection | Antagonism of cell mediated immunity by expression of: IL-4, anti-TNF, anti-IL-12, anti-IL-23, and/or anti-CD40L | Suppression of pro-inflammatory T cell priming; Generalized immunosuppression | IDO, sCD83, TGF-β, IL-19, IL-33, PDL-1, PDL-2, and/or anti-IFNγ |

Accordingly, in some embodiments, the cells used in the methods and/or compositions described herein are co-transfected with mRNA encoding one or more one or more immunomodulatory polypeptides selected from the group consistnosuppressive polypeptide is correlated with the stability of the mRNA within the cell and the stability of the expressed polypeptide. The stability of the mRNA and the efficiency of translation of the mRNA can be modulated by methods known to those of skill in the art, and include, but are not limited to 5' mRNA modifications, such as type 1 or type 0 capping, the use of cap analogs, such as ARCA, the use of ribonucleotide analogs, the use of 5' and 3' untranslated regions (UTRs), the presence or absence of a polyA tail, the length of a polyA tail, and the like. De novo translation of polypeptides encoded by the transfected mRNA may occur for up to 6, 8, 12, 18, 24 or more hours after transfection, depending on the stability of the mRNA. The half-life of the translated immunomodulatory polypeptide will depend upon its stability.

Preferably, the cells used in the methods and compositions disclosed herein are selected from the group consisting of B cells, B cell hybridomas, T cells, T cell hybridomas, macrophages, fibroblasts, dendritic cells and artificial antigen-presenting cells. Most preferably, the cells are dendritic cells. Methods for culturing and transfecting such cell are known in the art.

In another embodiment, a method is provided for treating or preventing an undesired immune response in a patient, comprising: administering to said patient, cells that transiently express one or more immunomodulatory polypeptides selected from the group consisting of an IL-4 receptor agonist, an IL-12 receptor antagonist, an IL-23 receptor antagonist, an IFN-γ receptor antagonist, an IFN-α receptor antagonist, and a TNF receptor antagonist.

As used herein, "transient expression of an immunomodulatory polypeptide" refers to instances where de novo translation of an immunomodulatory polypeptide of interest is detectable above background levels for at least one minute and up to, but preferably not exceeding, 48 hours after translation of that polypeptide begins. Most preferably, the polypeptide is transiently expressed for less than 36 hours, more preferably for less than 26, 24 or 22 hours and most preferably for less than 20, 18, 12, 8 or 6 hours. The length of time that the polypeptide is detectable after its translation may exceed 48 hours post administration, and will depend upon its stability.

Transient expression of an immunosuppressive polypeptide can be accomplished by a variety of mechanisms known to those of skill in the art. For example, cells can be transfected or transduced with a nucleic acid containing an expression cassette which comprises a coding sequence for an immunosuppressive polypeptide, wherein the coding sequence is operatively linked to a heterologous inducible promoter. Inducible mammalian promoters are known to those of skill in the art (see, e.g. Bitter et al. (1987) *Methods in Enzymology* 153: 516-544). Inducible promoters can be activated by external signals or agents. An inducible promoter is active when the inducer is present. The inducer may directly activate a promoter or inactivate a repressor of that promoter. For example, inducible systems endogenous to mammalian cells include promoters induced by heavy-metals (Brinster et al. Nature (1982) 296:39-42; Mayo et al. Cell (1982) 29:99-108; and Searle et al. Molecular and Cellular Biology (1985) 5:1480-1489), steroid hormones (Hynes et al. Proc. Natl. Acad. Sci. USA (1981) 78:2038-2042; Lee et al. Nature (1981) 294:228-232; and Klock et al. Nature (1987) 329:734-736), heat shock (Nouer, Heat Shock Response. Boca Raton, Fla., Ed. CRC, 1991) (reviewed in Mullick, A. and B. Massie Encyclopedia of Cell Technology pp. 1140-1164, 2000)) are well characterized. PCT publication WO2002/088346 discloses a cumate-inducible promoter. Additional inducible promoters are known in the art, and include, but are not limited to inflammation and hypoxia induced promoters.

Prokaryotic and insect inducible promoter systems have been adapted for regulated expression in mammalian cells. See, for example, Gossen et al. (1993) TIBS 18:471-475 and No et al. (1996) Proc. Natl. Acad. Sci. USA 93:3346-3351). The insect ecdysone-inducible promoter is tightly regulated with no detectable background expression in the absence of inducer. Ecdysone is suitable for use in vivo because it is a naturally occurring lipophilic steroid that can penetrate tissues, is inert in mammals and exhibits rapid clearance kinetics (No et al.). Gupta et al. (PNAS (2004) 101:1927-1932) discloses retroviral delivery of an ecdysone-inducible gene expression system under the control of a modified RNA polymerase III-specific U6 promoter.

The prokaryotic repressors from the lac and tet operons have been incorporated in eukaryotic inducible expression systems. Repression of expression is mediated by the repressor bound to operator sites placed downstream of the minimal promoter in the absence of inducer and repression is relieved on the addition of the inducer. (Brown et al. (1987) Cell 49:603-612; Hu and Davidson (1987) Cell 48:555-566; Blau and Rossi, Proc. Natl. Acad. Sci. USA (1999) 96:797-799; and Gossen et al. (1995) Science 268:1766-1769).

The RheoSwitch® Mammalian Inducible Expression System (New England Biolabs) allows induction and adjustable control of gene expression in mammalian cells. The promoter is tightly regulated, giving negligible levels of basal expression in the absence of inducer and greater than 10,000 fold induction when the inducer, RSL1 ligand is present. RSL1 ligand is a synthetic compound shown to be inert within all cell lines tested. Methods for construction of expression cassettes containing an inducible promoter operatively linked to a coding sequence of any polypeptide are known to those of skill in the art, as are methods for introducing such expression cassettes and vectors containing such expression cassette into homing cells.

The cells used in the methods and compositions described herein may transiently express the immunosuppressive polypeptide prior to the time of administration, at the time of administration and/or after administration. For example, in embodiments where expression of the immunomodulatory polypeptide is under the control of an inducible promoter, expression of the immunomodulatory polypeptide could be induced in vitro prior to administration and/or in vivo after administration. If expression is induced in vitro prior to administration, transient expression could be either complete or on-going at the time of administration. In cases where transient expression (i.e., de novo translation) of the immunosuppressive polypeptide is complete at the time of administration, the polypeptide should be stable enough to persist for at least 2, 4, 6, 8, 12, 18, 24 or more hours after administration. Alternatively, or in addition, transient expression can be induced one or more times after administration. Preferably, the cells transiently express (e.g., translated de novo protein) and/or contain the immunosuppressive protein of interest at the time they arrive at a secondary lymphatic tissue at or in the proximate vicinity of an undesired immune response.

In one embodiment, an isolated cell is provided, wherein the cell is transfected or transduced with an expression cassette or vector comprising a nucleic acid encoding a polypeptide selected from the group consisting of an IL-4 receptor agonist, an IL-12 receptor antagonist, an IL-23 receptor antagonist and a TNF receptor antagonist, wherein said nucleic acid is operatively linked to a heterologous inducible promoter, and said cell is selected from the group consisting of B cells, B cell hybridomas, T cells, T cell hybridomas, macrophages, dendritic cells and artificial antigen-presenting cells.

In preferred embodiments, the cells used in the methods and compositions described herein are able to home to (i.e., selectively accumulate in) one or more secondary lymphoid tissues in the proximate vicinity of an undesired immune response. The thymus and the bone marrow are primary lymphoid tissues. The secondary lymphoid tissues can be sites of lymphocyte activation by antigen. Secondary lymphoid tissue includes lymph nodes, spleen, gut associated lymphoid tissues such as tonsils, adenoids, appendix, and Peyer's patches; mucosa-associated lymphoid tissues and bronchial associated lymphoid tissues; as well as lymphoid tissue that develops at or near the site of an unwanted immune response, such as, but not limited to immune responses resulting in inflammation. As a nonlimiting example, the pancreatic lymph nodes are secondary lymphoid tissue in the proximate vicinity of the pancreas. The cells may selectively accumulate in secondary lymphoid tissue by selective recruitment and/or selective retention. As a non-limiting example of selective recruitment, cells may migrate toward a cytokine or chemokine gradient secreted by a secondary lymphoid tissue and/or a site of an undesired immune response. As a non-limiting example of selective retention, cells may arrive at a secondary lymphoid tissue at or in the proximate vicinity of an undesired immune response and be selectively retained in that tissue. In some cases, the mechanism of retention can be receptor-ligand interactions between the mRNA transfected cell and the secondary lymphoid tissue. As demonstrated in Example 1, below, the homing pattern may be affected by the route of administration. Preferably, the homing cells can be detected at the tissue(s) of interest at least 1 hour, 2 hours, 4 hours, 8 hours, 18 hours, 24 hours, 48 hours, or more following the time of administration.

In various embodiments of the invention, mRNA(s) encoding immunosuppressive polypeptides or expression cassette or vector encoding an inducible promoter operative linked to an immunomodulatory polypeptide are introduced into homing cells. As used herein, "homing cells" are cells that can selectively accumulate at one or more secondary lymphoid tissues in the proximate vicinity of the site of an undesired immune response. The ability to migrate to a site, tissue or organ of interest can be an inherent capability of a particular cell type, or the cell can be manipulated to migrate to sites of interest. For example, the route of administration can affect the homing properties of dendritic cells. Intradermal, subcutaneous, intralymphatic administration of DCs results in homing of DCs to local lymph nodes (Mackensen et al. Cancer Immunol Immunother 48:118-122; Morse et al. (1999) Cancer Res 59:56-58; Ridolfi et al. (2004) J. Transl. Med. 2:27; de Vries et al. (2005) Nat. Biotechnol. 23:1407-1413; Quillen et al. (2005) Eur. J. Nucl. Med. Mol. Imaging. 32:731-741; and Prince et al. J. Immunother 31:166-179). Previous studies have reported that DCs administered by i.v. injection home to spleen, lungs and liver. (Mackensen et al; Morse et al; Prince et al.; Eggert et al. (1999) Cancer Res. 59:3340-3345; Kim et al. (2001) J. Immunol. 166:3499-3505; Olasz et al. (2002) J. Immunol. Methods 260:137-148; Ahrens et al. (2005) Nat. Biotechnol. 23:983-987; Baumjohann et al. (2006) 211:587-597; and Horiguchi et al. (2007) J. Clin. Immunol. 127:598-604). Using very sensitive detection techniques, Example 1 of this specification demonstrates that DCs administered by i.v. injection selectively accumulate primarily to the spleen, pancreatic lymph nodes and mediastinal lymph nodes, and to a lesser extent to the mediastinal lymph nodes, and are relatively briefly found in the lungs and liver (see FIG. 1). In contrast, DCs administered by i.p. injection selectively accumulate primarily to the pancreatic lymph nodes and omental tissue, to a lesser extent to the mesenteric lymph nodes, lumbar lymph nodes, and liver, and to a minor extent to the spleen and inguinal lymph nodes (FIG. 1).

In preferred embodiments, the homing cell is a B cell, T cell, T cell hybridoma, B cell hybridoma, macrophage, fibroblast, artificial antigen presenting cell or a dendritic cell. Most preferably, the homing cell is a dendritic cell (DC). DCs can migrate through the lymphatics and/or venous system to secondary lymphoid tissues such as lymph nodes, including the pancreatic lymph nodes (PLN) and spleen. DCs can be modified to express other polypeptides that facilitate and/or alter homing properties. For example, DCs have been modified (e.g., using viral vectors or mRNA transfection) to express E/L Selectin, which allows the DCs to better migrate from blood vessels (for example, when administered intravenously) to multiple lymph nodes via high endothelial venules. See, for example, PCT publication WO2007096278, the contents of which is incorporated by reference. Optimized methods for transfecting DCs with mRNA are disclosed in the publication.

DCs and other cells useful in the methods and compositions of the invention can be modified to express a membrane homing polypeptide(s) in order to target a particular tissue. As used herein, a "membrane homing polypeptide" is a cell surface marker that is capable of interacting with or binding to a ligand present on another surface, such as the surface of a cell or the surface of the extracellular matrix.

In one embodiment, the membrane homing polypeptide is a selectin, integrin or chemokine receptor. Preferred selectins include E-selectin, L-selectin, P-selectin, the chimeric E/L-selectin, etc. Selectins are polypeptides that bind to sugar moieties on specific glycoproteins including but not limited to peripheral node addressin. Preferred integrins include CD11b, CD11c and a4b7. Expression of a4b7 aids in homing to the gut, and antibodies to this b1 integrin block type 1 diabetes. Preferred chemokine receptors include CCR4, CCR5, CCR7, CCR10, CXCR3 and CXCR4. Expression of CCR7 can aid in homing to lymph nodes and points of inflammation. CCR7, CXCR3, CCR5, and CXCR4 are particularly relevant for diabetes. Expression of CCR4 and CCR10 can aid in skin homing.

Antigen-specific T cells (including T cell lines and T cell hybridomas) and B cells (including B cell lines and B cell hybridomas) express a receptor that specifically recognizes an antigen, resulting in antigen-specific or tissue-specific retention properties. T cells and B cells can be isolated with (or engineered with) receptors that are specific for antigens associated with an autoimmune disease and/or a tissue affected by an autoimmune disease, which allows localized delivery of immunoregulatory polypeptides.

Non-limiting examples of antigens of interest include pancreatic islet cell epitopes (e.g., ICA512, ICA12), insulin, proinsulin, glutamic acid decarboxylase 65 (GAD65), IA-2, IA-2beta, HSP, glima 38, ICA69 and p52 for type 1 diabetes, myelin basic protein epitopes, proteolipid protein, myelin-associated glycoprotein and myelin oligo-dendrocyte glycoprotein for multiple sclerosis and other demyelinating diseases, collagen epitopes, hnRNP, A2/RA33, SA, filaggrin, keratin citrulline, cartilage proteins including gp39, RNA polymerase, for rheumatoid arthritis, desmoglein-3 protein (which is believed to be involved in the development of Pemphigus vulgaris), thyroid stimulating hormone (TSH) receptor (which is involved in the development of Grave's disease), thyroid peroxidase (which is involved in the development of Hashimoto's thyroiditis), acetylcholine receptor (which is involved in the development of myasthenia gravis), skin specific antigens, such as bowel-specific antigen for ulcerative colitis and tissue-specific epitopes or donor specific epitopes for transplanted tissues. Expression of CD103 can aid in gut homing as well as the selective induction of FoxP3 Tregs. Such sequences are known in the art, and additional sequences may be isolated.

T cells expressing a tissue-specific receptor to a tissue of interest can be isolated by methods known in the art. For example, Costa et al. (J Immunol (2001) 167:2379-2387) disclose myelin basic protein (MBP) specific $CD4^+$ T cells for delivery of therapeutic proteins to the central nervous system and treatment of experimental autoimmune encephalomyelitis (EAE), a mouse model for multiple sclerosis. Guichelaar et al. (J Immunol (2008) 180:1373-1381) disclose cartilage proteoglycan-specific $CD4^+$ T cells and their use in treating proteoglycan-induced arthritis, a mouse model of arthritis. Smith et al. (Gene Ther. (2003) 10:1248-57) disclose a collagen type II-specific T-cell hybridoma with joint-specific homing properties.

In one embodiment, T cells are transfected with RNA, DNA, viral vector, etc. encoding a tissue-specific receptor. Methods for isolating T cells and sequences encoding tissue-specific T cell receptors of interest are known in the art. See, for example, U.S. patent publication 20030091548, which discloses various T cell methods and PCT publication WO2007/065957, which discloses methods for expressing RNA encoding antigen-specific T cell receptors in T cells.

High-resolution techniques to detect homing patterns of cells transferred to humans, such as positron emission tomography, are known to those of skill in the art. For example the HSV1 thymidine kinase reporter genes and the 9-[4-[$^{18}$F]-fluoro-3-(hydroxymethyl)butyl]guanine can be combined with computed tomography to determine the homing patterns of therapeutic cells in humans. See, for example, Yaghoubi et al. (Nat Protoc (2007) 2:1752-1755).

Nucleic acids encoding an immunomodulatory polypeptide, homing polypeptide, etc., can be incorporated into an expression cassette, vector, viral vector, etc., for incorporation into the cells or to serve as templates for in vitro transcription of mRNA. Vectors that contain both a promoter and a cloning site into which a polynucleotide can be operatively linked are known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. Examples of vectors are viruses, such as lentivirus and retrovirus, adenovirus, adeno-associated virus, cosmid, plasmid, fungal vectors and other recombination vehicles typically used in the art that have been described for expression in a variety of eukaryotic and prokaryotic hosts, and may be used for gene therapy as well as for simple protein expression.

Polynucleotides can be inserted into vector genomes using methods known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. The mRNA, expression cassettes and vectors may further encode markers, such as fluorescent proteins, etc., which may be useful in tracking the migration patterns and persistence of the homing cells of the invention. Other means are known and available in the art.

Dendritic cells (DCs) are a preferred homing cell for use in the methods and compositions of the invention. Immature DCs can be isolated or prepared from a suitable tissue source containing DC precursor cells, which can be differentiated in vitro to produce immature DCs and mature DCs. (See PCT publication WO 2006/127150 and U.S. Ser. No. 11/918,076, the contents of which is incorporated by reference.) For example, a suitable tissue source can be one or more of bone marrow cells, peripheral blood progenitor cells (PBPCs), peripheral blood stem cells (PBSCs), and cord blood cells.

If desired, the number of dendritic precursor cells in animals, including humans, can be increased by pre-treating the subject with substances that stimulate hematopoiesis. Such substances include, but are not limited to G-CSF, GM-CSF and FLT3-L. The amount of hematopoietic factor to be administered may be determined by monitoring the cell differential of individuals to whom the factor is being administered. Typically, dosages of factors such as G-CSF and GM-CSF will be similar to the dosage used to treat individuals recovering from treatment with cytotoxic agents. As an example, GM-CSF or G-CSF can be administered for 4 to 7 days at standard doses prior to removal of source tissue to increase the proportion of dendritic cell precursors. U.S. Pat. No. 6,475,483 teaches that dosages of G-CSF of 300 micrograms daily for 5 to 13 days and dosages of GM-CSF of 400 micrograms daily for 4 to 19 days result in significant yields of dendritic cells.

For human applications, the preferred tissue source is peripheral blood mononuclear cells (PBMCs). The tissue source can be fresh or frozen. In some methods, the cells or tissue source can be pre-treated with an effective amount of a growth factor that promotes growth and differentiation of non-stem or progenitor cells, which are then more easily separated from the cells of interest. These methods are known in the art and described in Romani, et al. (1994) Exp. Med. 180:83 and Caux, C. et al. (1996) Exp. Med. 184:695.

In one method, the immature DCs are differentiated from peripheral blood mononuclear cells (PBMCs). In a preferred embodiment, the PBMCs or monocytes enriched therefrom are treated with an effective amount of granulocyte macrophage colony stimulating factor (GM-CSF) in the presence or absence of interleukin 4 (IL-4) and/or IL-13, so as to induce the differentiation of monocytes into immature DCs. Typically, PBMCs are cultured in the presence of GM-CSF and IL-4 for about 4-7 days to produce immature DCs.

In a preferred non-limiting method for making immature monocyte-derived DCs, human PBMCs are isolated from leukapheresis collections from a subject in need of treatment or from suitable donors. PBMCs are prepared by Ficoll-Histopaque density centrifugation and washed four times in PBS at room temperature. 2×10⁸ PBMCs are re-suspended in 30 ml AIM-V medium and monocytes are allowed to adhere to 150 cm³ plastic flasks for 2 hours at 37° C. Non-adherent cells are removed and remaining cells cultured in X-VIVO 15 medium, supplemented with GM-CSF (1000 U/ml) and IL-4 (1000 U/ml), for 5-7 days at 37° C., 5% CO₂. As an alternative to the Ficoll density gradient and adherence step, monocytes can be purified (enriched) by elutriation and then cultured in bags or flasks.

Either immature or mature DCs may be transfected with RNA or an expression cassette, or transduced with a viral vector containing an expression cassette. If transduced or transfected when immature, DCs may be administered to a subject while immature, or may be matured prior to administration.

Methods for DC maturation are known to those of skill in the art. For example, in the cytokine cocktail maturation method, immature DCs obtained by culture of monocytes in the presence of GM-CSF and IL-4 for 5-7 days can be cultured in medium containing a "cytokine cocktail" comprising of TNF-α (~10 ng/ml), IL-1β (~10 ng/ml), IL-6 (~100 ng/ml) and PGE₂ (~1 μg/ml) to produce mature DCs. (Jonuleit et al. Eur J Immunol (1997) 12:3135-3142) The above cytokine concentrations are preferred, but can vary substantially.

Dauer et al. (J Immunol (2003) 170:4069-4076) disclose a "FastDC" method for making mature monocyte-derived DCs within 48 hours. In this method, monocytes are incubated with GM-CSF and IL-4 for 24 hours followed by culture with a cytokine cocktail comprising TNF-α (1000 U/ml), IL-1β (10 ng/ml), IL-6 (10 ng/ml) and PGE₂ (1 μM) for 24 hours to produce mature DCs.

In an alternative "PME-CD40 ligand maturation" method, immature DCs can be phenotypically matured by overnight culture with TNF-α (~10 ng/ml), IFN-γ (1000 U/ml) and PGE₂ (~1 μg/ml). Mature DCs can then be harvested and electroporated with mRNA encoding one or more immunomodulatory polypeptides and mRNA encoding CD40 ligand (CD40L), and then cultured in media (preferably X-VIVO 15) containing ~800 U/ml GM-CSF and ~500 U/ml IL-4 for about 0-48 (preferably 4) hrs prior to harvest or formulation for administration. The above cytokine concentrations are preferred, but can vary substantially. (See U.S. patent publication 2007/0082400, the contents of which are incorporated by reference.)

Dendritic cells can be transfected with nucleic acids by methods known in the art, which include, but are not limited to calcium phosphate precipitation, microinjection or electroporation. In a preferred embodiment, DCs are transfected with mRNA using electroporation. As a nonlimiting example, prior to electroporation, DCs can be harvested and washed in PBS and then re-suspended in chilled Viaspan® (Barr Laboratories) at 4×10⁷/ml in 0.5 ml or 2.5×10⁷/ml in 0.2 ml and placed on ice. DCs can then be mixed with mRNA encoding one or more immunomodulators (about 1-6 μg RNA/10⁶ cells) and electroporated. Immediately or soon after electroporation, DCs can be washed in X-VIVO 15 medium, re-suspended in X-VIVO 15 supplemented with GM-CSF (800 U/ml) and IL-4 (500 U/ml) at 1×10⁶/ml and then cultured for about 4-24 hours at 37° C.

The compositions and methods disclosed herein are useful for treating or preventing undesired immune responses, such as immune responses against therapeutic compositions (e.g., therapeutic proteins, gene therapy vectors, stem cells, etc.), transplant rejection, allergy and autoimmune diseases, including, but not limited to insulin dependent diabetes mellitus, multiple sclerosis, rheumatoid arthritis, psoriasis, systemic lupus erythematosus, ulcerative colitis chronic obstructive pulmonary disease and asthma. In preferred embodiments, the autoimmune disease is insulin dependent diabetes mellitus. In one embodiment, overt diabetes is prevented by initiating treatment when anti-islet antibodies are detected in a patient. In particular, such an anti-islet antibody may be specific for glutamate decarboxylase (GAD), insulinoma associated peptide-2 (IA-2) or insulin.

The methods and compositions of the invention are useful for therapeutic purposes and thus are intended to prevent, cure, or alleviate at least one symptom of a disease or disorder caused by the dysfunction or undesired function of an immune response, such as, but not limited to autoimmune diseases, allergy and transplant rejection. The prevention of autoimmune disease can be accomplished by administration of the cells of the invention prior to the development of overt disease. Alleviation of disease or unwanted immune responses includes instances where expression of immunomodulatory polypeptides by the cells stabilize or improve the clinical symptoms of the patient. A symptom of a disease or disorder is considered to be reduced if an undesired symptom is decreased, or improved, as appropriate, by at least 10%, 20%, 30%, 40%, 50%, 70%, 90% or more in comparison to an appropriate control, such as in comparison to the symptom prior to treatment or in comparison to the expected severity of the symptom, where the treatment is intended to be preventive. One of skill is familiar with techniques and criteria for evaluating changes in symptoms. Symptoms of diseases or disorders caused by the dysfunction or undesired function of an immune response are known to those in the art and include the following: abnormal histology of a transplanted tissue; abnormal function of a transplanted tissue; brief length of survival time following an event such as, for example, diagnosis or transplantation; abnormally or undesirably high or low level or number of indicator protein(s) or other compound(s) in the blood, such as undesired antibodies or undesired cells (e.g., antigen-specific T cells); abnormally or undesirably high or low level or number of indicator cells in the blood or elsewhere in the body, e.g., an undesirably low level or number of regulatory T cells, so that an undesired immune response is initiated or maintained.

Where appropriate, in vivo immunosuppression or tolerance to a transplanted cells or tissue may be measured using in vitro assays, such as, for example, a mixed lymphocyte reaction using cells isolated from a subject. Similarly, tolerance and/or immunosuppression achieved in cells ex vivo may also be measured in ex vivo assays using various types of cells, such as, for example, dendritic cells, T cells, or B cells. If tolerization or tolerance and/or immunosuppression is measured using an ex vivo method, tolerization or tolerance is considered to have occurred if the response of the cells to an immune stimulus is decreased by at least 10%, 20%, 30%, 40%, 50%, 70%, 90% or more in comparison to an appropriate control. Suitable assays directly or indirectly measure immune response and are known in the art; they include, but are not limited to: mixed lymphocyte reaction assays; cytotoxicity assays; antibody titer assays; assays for the production of IL-4 and/or IL-10; assays for the production of TGF-β; evaluation of cell surface markers; and assays for the expression of Foxp3.

The cells can be administered in any suitable manner, often with pharmaceutically acceptable carriers. Autologous or allogenic cells may be used. The cells may be administered in any physiologically acceptable medium. In one embodiment, the cells are cryopreserved in 5-20% DMSO, 5% dextrose and autologous serum. As is familiar to those of skill in the art, dosage of the cells of the present invention to be administered in vivo is determined with reference to various parameters, including the species of the host, the age, weight and disease status. Dosage also depends upon the location to be targeted within the host, e.g. the site of transplantation of tissue from a donor. For example, direct targeting to the site of inserted tissue may require different dosages than administration into the blood stream of a mammalian host. The dosage is preferably chosen so that administration causes an effective result, which can be measured by molecular assays or by monitoring a suitable symptom in the subject. Dosages may range from about at least $1\times10^4$ cells to about at least $1\times10^9$ cells per administration. In some embodiments, the dosage ranges from about $5\times10^5$ cells to about $5\times10^7$ cells. Optionally, more than one dose may be administered.

Optimal routes of administration may be determined by one of ordinary skill in the art, and include, but are not limited to, conventional and physiologically acceptable routes, such as, intravenous, intraperitoneal, intramuscular, intra-articular, intradermal, subcutaneous and intranodal administration. In preferred embodiments, administration is intravenous.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. See, for example, Sambrook et al. Molecular Cloning: A Laboratory Manual, 3rd edition (2001); Current Protocols in Molecular Biology (Ausubel et al. eds. (1988)); the series Methods In Enzymology (Academic Press, Inc.); PCR: A Practical Approach (M. MacPherson et al. IRL Press at Oxford University Press (1991)); PCR 2: A Practical Approach (MacPherson, Hames and Taylor eds. (1995)); Current Protocols in Immunology, eds. Coico et al. (Wiley, Hoboken, N.J.); Antibodies, A Laboratory Manual (Harlow and Lane eds. (1988)); Using Antibodies: A Laboratory Manual (Harlow and Lane eds. (1999)); and Animal Cell Culture (Freshney ed. (1987)).

As used in the specification and claims, the singular forms "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but do not exclude additional elements. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. Polypeptides or protein that "consist essentially of" a given amino acid sequence are defined herein to contain no more than three, preferably no more than two, and most preferably no more than one additional amino acids at the amino and/or carboxy terminus of the protein or polypeptide. Nucleic acids or polynucleotides that "consist essentially of" a given nucleic acid sequence are defined herein to contain no more than ten, preferably no more than six, more preferably no more than three, and most preferably no more than one additional nucleotide at the 5' or 3' terminus of the nucleic acid sequence. "Consisting of" shall mean excluding more than trace elements of other ingredients and substantial method steps for administering the compositions of this invention. Embodiments defined by each of these transition terms are within the scope of this invention.

The term "isolated" means separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragment(s) thereof, does not require "isolation" to distinguish it from its naturally occurring counterpart. In addition, a "concentrated", "separated" or "diluted" polynucleotide, peptide, polypeptide, protein, antibody, or fragment(s) thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragment(s) thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as its glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature. A mammalian cell, such as dendritic cell is isolated if it is removed from the anatomical site from which it is found in an organism.

"Enriched" refers to a composition comprising cells present in a greater percentage of total cells than is found in the tissues where they are present in an organism. For example, isolated cells may be enriched by further purification and/or expansion.

The term "antigen presenting cells (APCs)" refers to a class of cells capable of presenting one or more antigens in the form of peptide-MHC complex recognizable by specific effector cells of the immune system. APCs include macrophages, B-cells and dendritic cells. As used herein, "artificial antigen presenting cell" refers a living cell which has been engineered to express MHC Class I and/or II molecules and/or other molecules required for costimulation of CD4+ and CD8+ T cells.

The term "dendritic cells (DCs)" refers to a member of a diverse population of morphologically similar cell types found in a variety of lymphoid and non-lymphoid tissues (Steinman (1991) Ann. Rev. Immunol. 9:271-296). Dendritic cells, also referred to as professional antigen presenting cells, have a high capacity for sensitizing MHC-restricted T cells. Dendritic cells may be recognized by function, by phenotype and/or by gene expression pattern, particularly by cell surface phenotype. Mature dendritic cells are characterized by their distinctive morphology, high levels of MHC-class II and costimulatory molecule expression and ability to present antigen to CD4+ and/or CD8+ T cells, particularly to naïve T cells.

The cell surface of mature DCs has veil-like projections, and is characterized by expression of the cell surface markers CD11c and MHC class II. Mature DCs are positive for CD80, CD83 and CD86. Immature DCs express low levels of MHC class II, and are capable of endocytosing and processing antigens for presentation in complex with MHC class II molecules.

Dendritic cells are the most potent and preferred APCs in the organism. While the dendritic cells can be differentiated from monocytes, they possess distinct phenotypes. For example, a particular differentiating marker, CD14 antigen, is not found in dendritic cells but is possessed by monocytes. Also, mature dendritic cells are not phagocytic, whereas the monocytes are strongly phagocytosing cells. It has been shown that mature DCs can provide all the signals necessary for T cell activation and proliferation.

The terms "polynucleotide", "nucleic acid" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-stranded, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In addition to a native nucleic acid molecule, a nucleic acid molecule of the present invention may also comprise modified nucleic acid molecules. As used herein, mRNA refers to an RNA that can be translated into a protein in the cells of the invention. Such mRNAs typically are capped and have a ribosome binding site (Kozak sequence) and a translational initiation codon.

"Under transcriptional control" is a term understood in the art and indicates that transcription of a polynucleotide sequence, usually a DNA sequence, depends on its being operatively linked to an element which contributes to the initiation of, or promotes, transcription. "Operatively linked" refers to a juxtaposition wherein the elements are in an arrangement allowing them to function. For example, a coding sequence for a polypeptide of interest may be both operatively linked to, and under the transcriptional control of a promoter (e.g., an inducible promoter or T7 promoter).

By "promoter" is meant at least a minimal sequence that is sufficient to direct transcription. Promoters for use in or with the invention can be constitutive or inducible, as appropriate (see, e.g. Bitter et al. (1987) *Methods in Enzymology* 153: 516-544). Inducible promoters are activated by external signals or agents. Other promoter elements can include those which are sufficient to provide control of promoter-dependent gene expression for specific cell-types, tissues or physiological conditions; such elements may be located in the 5', 3', or intronic regions of the gene.

As used herein, "to transfect" or "transfection" refers to the introduction of one or more exogenous nucleic acids or polynucleotides, such as DNA or RNA, into a eukaryotic cell. Transfection includes introduction in such a manner that a protein encoded by the nucleic acid or polynucleotide can be expressed. Transfection methods are known in the art and include a variety of techniques such as electroporation, biolistics delivery, nucleic acid delivery vehicles, and various other techniques known to those of skill in the art. Examples of nucleic acid delivery vehicles are liposomes, biocompatible polymers, including natural polymers and synthetic polymers, lipid-based and cationic ion based nucleic acid delivery complexes, lipoproteins, polypeptides; polysaccharides, lipopolysaccharides, artificial viral envelopes, metal particles, microbeads, microspheres, bacteria, viral vectors or viruses, such as baculovirus, adenovirus and retrovirus/lentivirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression. A number of vectors are capable of mediating transfer of genes to mammalian cells, as is known in the art and described herein. Stable maintenance of an introduced polynucleotide typically requires that the polynucleotide either contains an origin of replication compatible with the host cell or integrates into a replicon of the cell such as an extrachromosomal replicon (e.g., a plasmid) or a nuclear or mitochondrial chromosome. DNA, vectors and expression cassettes can generally be maintained in dendritic cells for relatively long periods, as these cells do not divide and thereby "dilute out" the DNA, vector, or expression cassette. Transfected mRNA does not integrate into the host genome nor replicate independently. In contrast to DNA, mRNA is more labile and is eventually degraded within the cell and its half life is sequence dependent.

In preferred embodiments of the invention, cells are transiently transfected with RNA using electroporation. Methods of RNA electroporation are well-known in the art. Generally, mRNA does not become a permanent part of the genome of the cell, either chromosomal or extrachromosomal. Any other methods that could be used to transiently express a desired protein are also contemplated within the scope of the invention. The methods do not involve permanent alteration of the genome (i.e., do not result in heritable genetic change to the cell) and thus avoid the disadvantages associated with the use of viruses, such as, for example, retroviruses and adenoviruses.

The term "vector" refers to a plasmid, virus, or other vehicle known in the art that can be manipulated by insertion or incorporation of a polynucleotide. Such vectors can be used for genetic manipulation (i.e., "cloning vectors") or can be used to transcribe and/or translate the inserted polynucleotide ("expression vectors"). A vector generally contains at least an origin of replication for propagation in a cell and a promoter. Control elements present within an expression vector, including expression control elements as set forth herein, are included to facilitate proper transcription and translation (e.g., splicing signals for introns, maintenance of the correct reading frame of the gene to permit in-frame translation of mRNA, stop codons, etc.). The term "control element" as used herein includes, at a minimum, one or more components whose presence can influence expression; the term "expression control element" as used herein refers to one or more nucleic acid sequences that regulates the expression of a nucleic acid sequence to which it is operably linked. An expression control element operably linked to a nucleic acid sequence controls transcription and, as appropriate, translation of the nucleic acid sequence. Thus an expression control element can include, as appropriate, promoters, enhancers, transcription terminators, and/or a start codon (e.g., ATG) in front of a protein-encoding gene. Vectors can also include additional components such as, for example, leader sequences and fusion protein sequences. "Operably linked" refers to a juxtaposition wherein components are in a relationship permitting them to function in their intended manner.

A "viral vector" is a recombinantly produced virus or viral particle that comprises a polynucleotide to be delivered into a host cell, either in vivo, ex vivo or in vitro. Examples of viral vectors include retroviral and lentiviral vectors, adenoviral vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Zaks et al. (1999) Nat. Med. 7:823-827. In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome, when the host cell is actively dividing. The virus can enter the host cell via its normal mechanism of infection or be modified such that it binds to a different host cell surface receptor or ligand to enter the cell. As used herein, "retroviral vector" refers to a viral particle capable of introducing exogenous nucleic acid into a cell through a viral or viral-like entry mechanism. Similarly, 'lentiviral vector' refers to an HIV-based retroviral vector that, unlike most other retroviral vectors, allows DNA integration in the genome of non-dividing or slowly dividing cells.

In aspects where gene transfer is mediated by a DNA viral vector, such as an adenovirus (Ad), pseudo adenoviral or adeno-associated virus (MV), vector construct refers to the polynucleotide comprising the viral genome or part thereof, and a transgene. Adenoviruses (Ads) are a relatively well characterized, homogenous group of viruses, including over 50 serotypes. (See, e.g., WO 95/27071). Ads are easy to grow and do not require integration into the host cell genome. Recombinant Ad-derived vectors, particularly those that reduce the potential for recombination and generation of wild-type virus, have also been constructed. (See, WO 95/00655 and WO 95/11984). Wild-type MV has high infectivity and specificity integrating into the host cell's genome. (See, Hermonat and Muzyczka (1984) Proc. Natl. Acad. Sci. USA 81:6466-6470 and Lebkowski et al. (1988) Mol. Cell. Biol. 8:3988-3996).

DNA vectors that contain both a promoter and a cloning site into which a polynucleotide can be operatively linked are known in the art. Such vectors are capable of transcribing RNA in vitro or in vivo, and are commercially available from sources such as Stratagene (La Jolla, Calif.), New England BioLabs (Beverly, Mass.) and Promega Biotech (Madison, Wis.).

A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity is determined using the well known BLAST alignment program and the default parameters. Alternative programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following World Wide Web address: ncbi.nlm.nih.gov/cgi-bin/BLAST.

A "subject" or "patient" refers to a mammal, more preferably a human. Mammals include, but are not limited to, mice, simians, humans, farm animals, sport animals, and pets.

A "pharmaceutical composition" is intended to include the combination of an active agent with a carrier, inert or active, making the composition suitable for diagnostic or therapeutic use in vitro, in vivo or ex vivo. Pharmaceutical compositions comprising the cells of the invention can comprise, physiological suitable buffers, culture media, cyropreservatives, DMSO, polyols, such as dextrose, serum (preferably autologous serum), etc.

An "effective amount" is an amount sufficient to exert beneficial or desired results, such as suppression of an undesired immune response, treatment, prevention or amelioration of a medical condition (e.g., autoimmune disease, transplant rejection). An effective amount can be administered in one or more administrations, applications or dosages. Suitable dosages will vary depending on body weight, age, health, disease or condition to be treated and route of administration.

The following examples are put forth so as to provide those of ordinary skill in the art with a complete disclosure and description of how to make and use the invention, and are not intended to limit the scope of what is regarded as the invention. It is to be understood that this invention is not limited to the particular methodology, protocols, cells lines, animal species or reagents described, as such may vary.

EXAMPLES

Example 1

Effect of Route of Administration on Biodistribution of Murine Bone Marrow-Derived DCs Bone marrow derived murine DCs were either transduced to express a GFP-luciferase fusion protein (as described in Creusot et al. (2008) Clin. Immunol. 127:176-187) or obtained from 10-12 week old luciferase-transgenic mice. Briefly, bone marrow derived murine DCs were prepared as follows. Bone marrow cells were obtained from the tibia, femur and pelvis of 8-10 week old female donor mice, after crushing with a mortar and pestle (under sterile conditions) and Ficoll separation (Histopaque-1119). Recovery was approximately $70 \times 10^6$ cells per mouse. Following red blood cell lysis, bone marrow cells were depleted of T cells, B cells and granulocytes cells by AutoMACS™ (Miltenyi) negative selection using biotinylated anti-CD3$^+$, anti-B220$^+$, anti-Gr-1$^+$ (eBioscience) and anti-biotin microbeads (Miltenyi). The remaining bone marrow cells (~10% of original count) were plated in 6-well plates ($2 \times 10^6$ cells/well in 3 ml) and differentiated into dendritic cells by culture in complete RPMI (10% FCS, L-Gln, 1× Pen/Strep, 1× sodium pyruvate, 1× non-essential amino acids, 1× beta-mercaptoethanol), supplemented with recombinant mouse 10 ng/ml GM-CSF and 10 ng/ml IL-4 (Peprotech). On the morning of the third day of differentiation, 2 ml of medium was removed and replaced with 3 ml fresh medium. On the morning of the fifth day, 2 ml of medium was removed, the cells were then resuspended, split 1:2 and plated with 3 ml fresh medium. On day 6, the murine dendritic cells were harvested (two washes and incubations with cold PBS/EDTA) and counted. Typically, 3-4 fold more cells were recovered than plated on day 0, with a good purity (75-95% CD11c$^+$ CD11b$^+$).

For GFP-luciferase transduced DCs, bone marrow derived murine dendritic cells were prepared as described above through the third day of differentiation. On day 4 of culture as described above, murine dendritic cells were infected with lentiviral particles (multiplicity of infection of 15) expressing a GFP-luciferase fusion protein in the presence of 10 µg/ml protamine sulfate (Sigma). After 16-24 hours incubation with virus, the medium was changed. DCs were collected on day 6 and resuspended in PBS for administration to NOD mice.

$5 \times 10^6$ Luciferase (Luc$^+$) transduced or transgenic DCs were administered to NOD or FVB mice by intravenous (i.v.)

injection or intraperitoneal (i.p.) injection. Three to five days after administration, the mice were sacrificed and the level of luminescence was assessed in the following tissues: spleen, pancreatic lymph nodes (LN), mesenteric LN, lumbar LN, inguinal LN, mediastinal LN, cervical LN, thymus, pancreas, omental tissue, lungs and liver. As shown in FIG. 1, the homing pattern of DCs is affected by the route of administration. Homing to the pancreatic lymph nodes was improved by i.p. injection as compared to i.v. injection, but remained very specific by either route relative to most other lymph nodes. In addition, a great fraction of DCs administered by i.p. injection are found in and around the milky spots of the pancreas-associated omental tissue. Similar biodistributions were observed in BALB/c and NOD.B10 mice.

Example 2

Optimization of IL-4 RNA for Expression in Human Dendritic Cells

The murine IL-4 cDNA, either with or without the addition of the 3' UTR of the simian rotavirus gene 6 downstream of the IL-4 coding sequence, was inserted in into a plasmid vector designed for in vitro transcription from a T7 promoter. The sequence and features of the vector are shown in SEQ ID NO:1. Nucleotides 2487-2506 of SEQ ID NO:1 correspond to the T7 promoter. Nucleotides 2551-2970 of SEQ ID NO:1 corresponds to the mIL-4 coding sequence, and SEQ ID NO:2 corresponds to the mIL-4 protein. Nucleotides 2983-03121 of SEQ ID NO:1 corresponds to the Rotavirus gene 6 3' UTR element. Nucleotides 3128-3191 of SEQ ID NO:1 corresponds to an oligo T stretch. mRNA, was synthesized by in vitro transcription (IVT) of the linearized plasmid shown in using mMessage mMachine™ T7 Ultra kits (Ambion) following the manufacturer's directions. The RNA was capped according to the manufacturer's (Epicenter Biotechnologies) directions with: 1) ARCA, 2) m7G using ScriptCap™ m7G Capping System to produce type 0 capping, or 3) m7G using ScriptCap™ m7G Capping System with the addition of ScriptCap™ 2'-O-methyltransferase to produce type 1 capping. Capped RNA was purified using a RNAeasy™ Kit (Qiagen) according to the manufacturer's directions. IVT RNA was polyadenylated using A-Plus™ Poly(A) Tailing kit (Epicenter) according to the manufacturer's directions. Polyadenylated RNA was purified using an RNeasy column (Qiagen). RNA was eluted in water and stored in individual size aliquots below −150° C. prior to electroporation into DCs.

Monocyte-derived immature human dendritic cells were prepared and electroporated with RNA as follows. Human peripheral blood monocytic cells (PBMCs) were isolated from leukapheresis collections from healthy volunteers by Ficoll-histopaque density centrifugation. PBMCs were re-suspended in AIM-V medium (Invitrogen) and allowed to adhere to 150 cm$^3$ plastic flasks for 2 hours at 37° C. Non-adherent cells were removed and remaining cells cultured in X-vivo 15 medium, supplemented with 1000 U/ml GM-CSF (Leukine) and 1000 µml IL-4 (R&D systems), for 6 days at 37° C., 5% $CO_2$.

Prior to electroporation, the DCs were harvested and washed in PBS and then re-suspended in chilled Viaspan. DCs were mixed with various in vitro transcribed IL-4 mRNAs prepared as described in Example 2 (2 or 4 µg RNA per million cells). This mixture was placed in a 4 mm gap electroporation cuvette and electroporated using a BioRad Gene Pulser X-Cell apparatus (5-7 minute exponential decay pulse, Voltage: 300V; Capacitance: 150 µF, Resistance: 100 Ohms).

Immediately after electroporation, the DCs were washed in X-vivo-15 medium and finally re-suspended in X-vivo-15 supplemented with 800 U/mL GM-CSF and 500 U/mL IL-4 at 1×10$^6$/ml.

Figure 3:
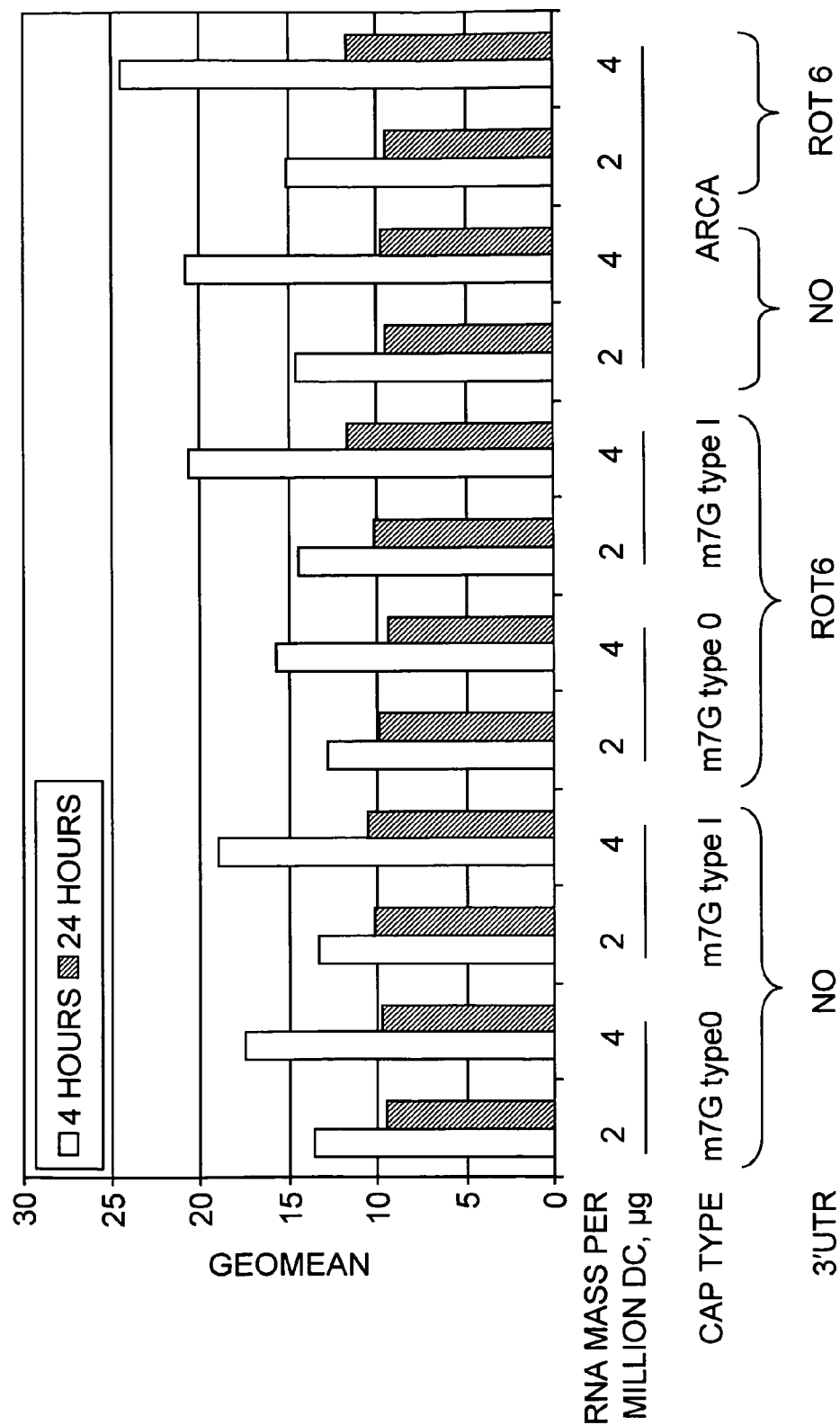
FIG. 3 shows the effect of mRNA modifications, such as various types of 5' capping (e.g., ARCA, m7G type 1 and m7G type 2) and the presence or absence of the rotavirus gene 6 3'UTR on the Geomean for mRNA transfected human immature dendritic cells expressing murine IL-4 at 4 and 24 hrs post transfection.

Following electroporation, the cells were cultured for 4 or 21 hours prior to measuring IL-4 protein levels by ELISA. As shown in FIGS. 2 and 3, IL-4 expression was enhanced by the presence of the rotavirus gene 6 3' UTR. These experiments demonstrate that the levels and longevity of IL-4 RNA expression can be manipulated by modifications to the mRNA structure.

Figure 4:
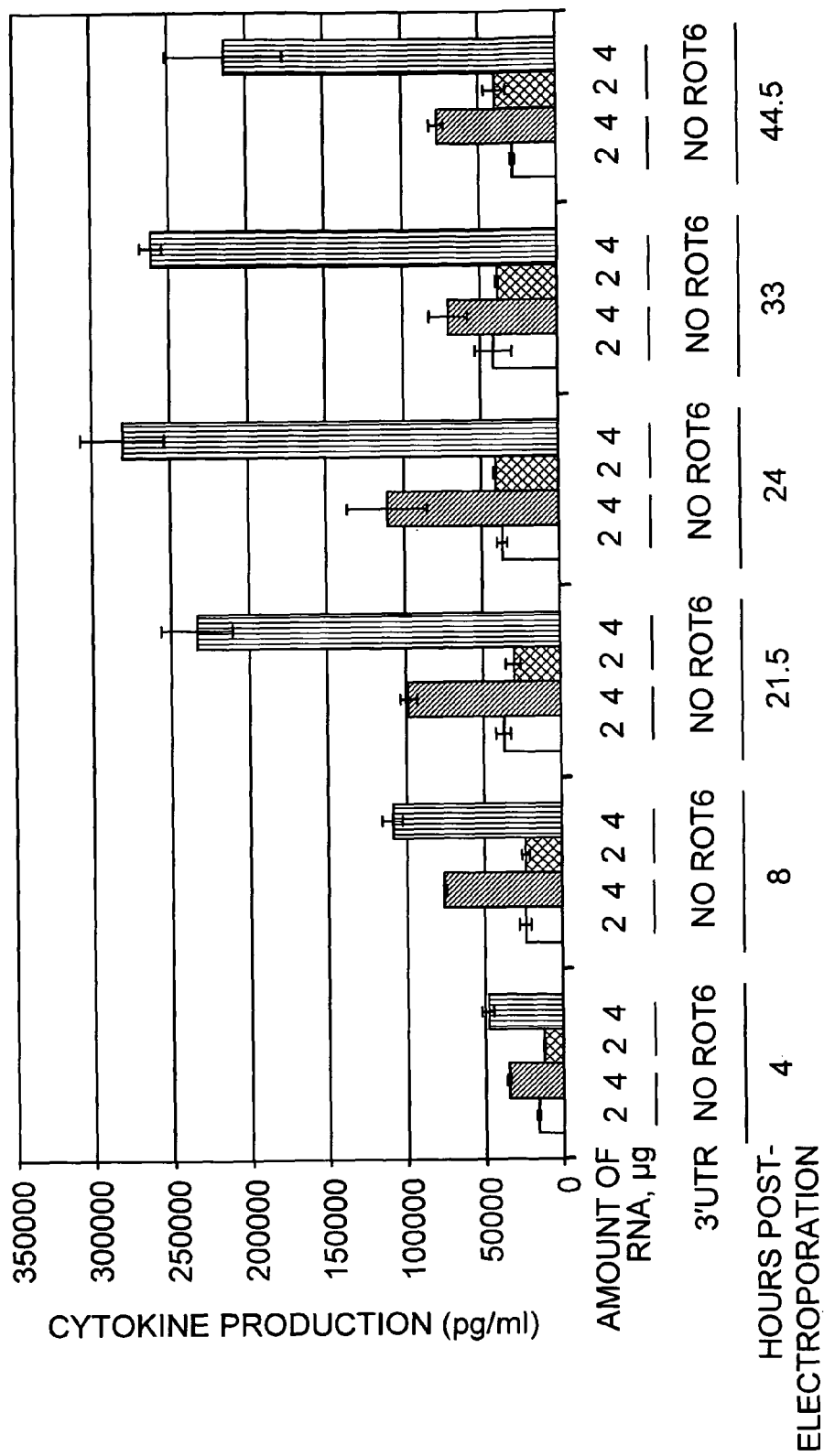
FIG. 4 shows the effect of the presence or absence of the Rotavirus gene 6 3' UTR (Rot6) in mRNA downstream of the IL-4 coding sequence on the level and duration of secretion of murine IL-4 from human immature. DCs electroporated with either 2 or 4 μg of RNA per million DC. Each IL-4 RNA was post-transcriptionally capped with m7G (type 1) and poly-adenylated.

The time course of IL-4 protein expression was next evaluated at 4, 8, 21.5, 24, 33 and 44.5 hours post-electroporation. FIG. 4 shows that inclusion of the 3'-UTR from simian rotavirus 6 downstream of the IL-4 coding region improves the overall level of IL-4 secretion. IL-4 accumulates in the supernatant until 24 hrs post electroporation, after which no further increase in IL-4 was detected.

Example 3

Transduction of Murine Dendritic Cells with Lentiviral IL-4 Constructs

Nucleic acid encoding murine IL-4 and GFP were sub-cloned into the lentiviral vector described by Breckpot et al. (Journal of Gene Medicine, 2003, 5(8) 654-67). Bone marrow derived murine dendritic cells were prepared as described in Example 2 through the third day of differentiation. On day 4 of culture as described above, murine dendritic cells were infected with lentiviral particles (multiplicity of infection of 15) expressing IL-4 and GFP (on a bicistronic mRNA) in the presence of 10 µg/ml protamine sulfate (Sigma). After 16-24 hours incubation with virus, the medium was changed. DCs were collected on day 6 and resuspended in PBS for administration to NOD mice.

Example 4

Expression of IL-4 in Lentiviral Transduced Versus RNA-Electroporated Murine DCs Bone marrow derived murine DCs were prepared as described in Example 1. Bone marrow derived murine DCs were either transduced with a lentiviral vector expressing both IL-4 and GFP (IL4-IRES-GFP), or electroporated with IL-4 RNA or GFP RNA. Prior to electroporation, the DCs were washed 3 times in cold OptiMEM and resuspended at 5×10$^6$ cells/0.2 ml. 200 µL cells were aliquoted in chilled tubes, and mRNA (m7G type 1 capped and polyadenylated) was added (2 or 4 µg RNA per 5×10$^6$ cells). The cells and mRNA were then transferred into chilled 4 mm cuvettes and electroporated (Voltage: 300V; Capacitance: 150 µF, Resistance: 100Ω).

Figure 5:
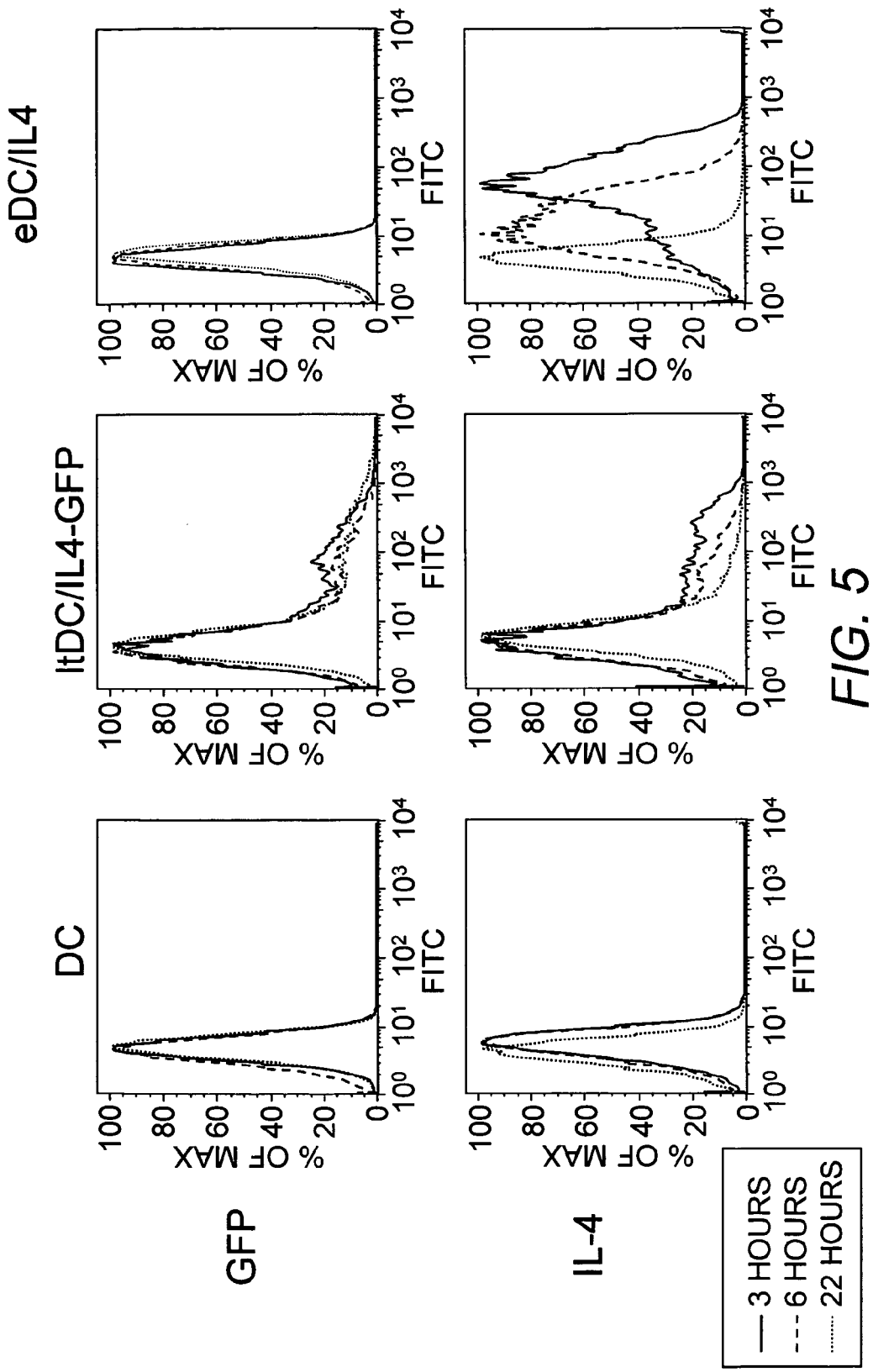
FIG. 5 shows flow cytometry results measuring intracellular GFP (top row) or IL-4 (bottom row) protein expression in control DCs (DC), DCs transduced with an IL-4 and GFP lentiviral expression vector (ltDC/IL4-GFP) or DCs electroporated with IL-4 RNA (eDC/IL-4).

Following electroporation or transduction, the DCs were cultured in vitro for 3, 6 or 22 hours and expression of IL-4 and GFP was assessed by intracellular staining with anti-IL4 (Perkin Elmer) and flow cytometry. Of these time points, IL-4 expression was highest at 3 hours for both lentivirally transduced DCs (ltDC/IL4-GFP) and IL-4 RNA electroporated DCs (eDC/IL4). However, IL-4 expression was absent at 22 hours in IL-4 RNA electroporated DCs, while expression was low yet detectable in lentiviral transduced DCs (FIG. 5). The data suggest that expression decreases faster in electroporated DCs as compared to virally transduced DCs. However, it should be noted that GFP remains in the cell while IL-4 is secreted. Secreted IL-4 is not detected by flow cytometry.

Figure 6A:
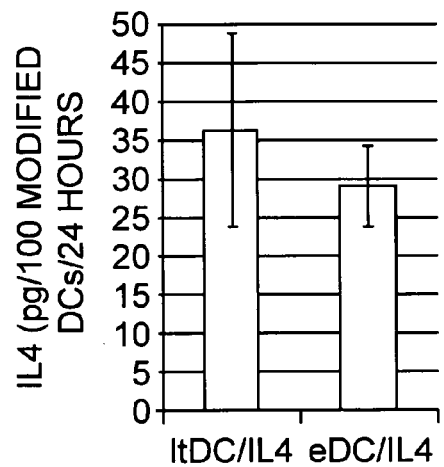
FIG. 6A shows the level of IL-4 secretion per 100 cells over 24 hrs.
Figure 6B:
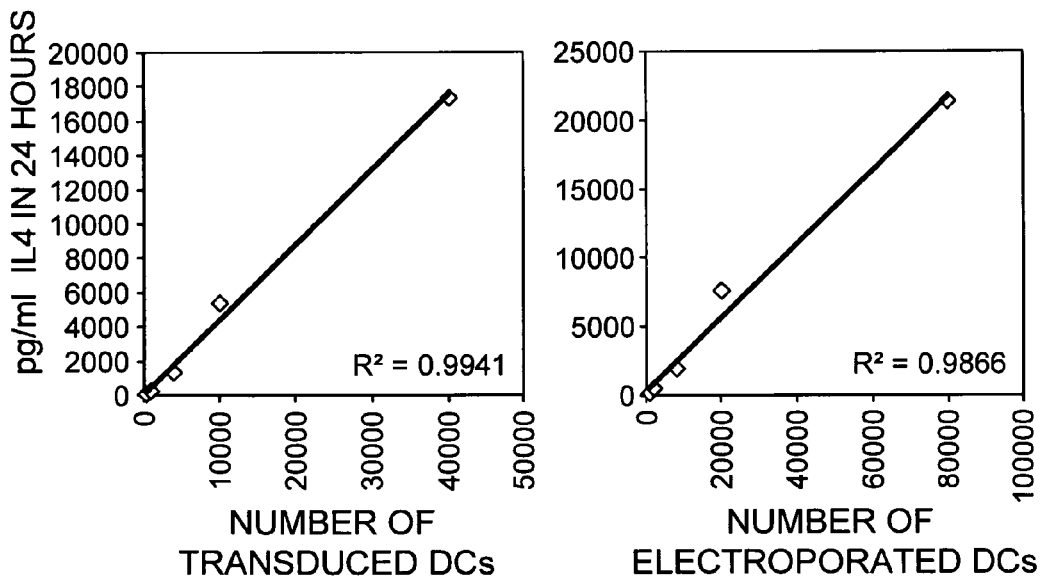
FIG. 6B shows graphs of the amount of IL-4 secreted over 24 hours per number of transduced DCs (left; ltDC/IL-4) or electroporated DCs (right; eDC/IL-4).

In a second experiment, DC electroporated with m7G type 1 capped and polyadenylated murine IL-4 RNA (eDC/IL-4) were compared to lentiviral IL-4 transduced DCs (ltDC/IL4) for transduction efficiency (number of cells expressing IL-4 by intracellular staining) and overall secretion of cytokine per culture. For electroporation, 6 µg murine IL-4 RNA was used per million DCs. Per number of cells seeded for analysis, lentiviral and RNA electroporated DC secrete equivalent levels of IL-4 after 24 hrs (FIG. 6A). A comparison of the number of cells expressing protein shows that lentiviral transduction is less efficient (40% transduction) than RNA electroporation (80% transduction) in achieving a high frequency of cells with the potential to secrete IL-4 (FIG. 6B). The total secreted IL-4 is proportional to the number of DC seeded in culture.

Example 5

Comparative Analysis of IL-4 Lentiviral Transduced Versus IL-4 RNA Electroporated Dc to Prevent the Onset of Overt IDDM Murine bone marrow derived DCs were harvested on day 6 as described in Example 1. Prior to electroporation, the cells were washed three times in cold OptiMEM and resuspended at $5 \times 10^6$ cells/0.2 ml. 200 µl cells were aliquoted in chilled tubes, and either 10-30 µg GFP mRNA or 30 µg IL-4 mRNA (each m7G type 1 capped and polyadenylated) was added. The cells and mRNA were transferred to chilled 4 mm cuvettes and electroporated (Voltage: 300V, Capacitance: 150 µF; Resistance: 100Ω). The concentration of the electroporated cells was adjusted with PBS to approximately $5 \times 10^6$ cells/ml. The cells were counted again to confirm the concentration, washed in PBS and resuspended in PBS ($1 \times 10^6$ cells/0.2 ml) for immediate injection into intravenously into mice as described below.

Figure 7:
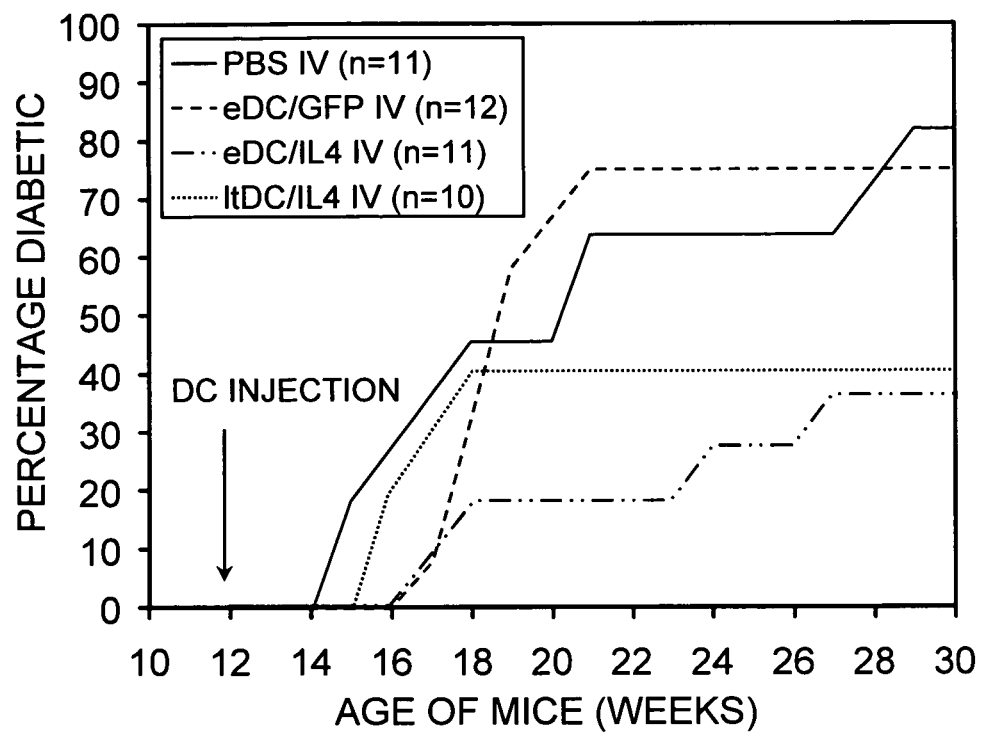
FIG. 7 shows the inhibitory effect on diabetes in NOD mice of a single administration of DCs expressing IL-4 via transfected mRNA (eDC/IL-4) or a lentiviral vector (ltDC/IL-4) as compared to DCs expressing GFP via transfected mRNA (eDC/GFP) or mice treated with phosphate buffered saline (PBS).

12-week old female non-obese diabetic (NOD) mice received a single intravenous injection (into the lateral tail vein) of $1 \times 10^6$ murine DC in 0.2 ml, either electroporated with m7G type 1 capped and polyadenylated murine RNA (eDC/IL-4) (prepared as described above) or lentivirally transduced (LtDC/IL4; prepared as described in Example 3). Control mice received DC electroporated with RNA encoding green fluorescent protein (eDC/GFP) or PBS. Blood glucose was measured weekly. Mice with glucose levels greater than 250 mg/dl for two consecutive weeks were considered diabetic. FIG. 7 shows that eDC/IL-4 DC significantly reduced the incidence of overt diabetes compared to either the PBS or eDC/GFP controls. eDC/IL-4 reduced the overall incidence of diabetes to the same level as mice treated with IL-4 lentiviral transduced DC (ltDC/IL-4). However, eDC/IL-4 are superior in delaying the onset of disease. Specifically, a single i.v. injection of 12-week-old NOD mice with DCs transfected IL-4 mRNA as described herein is effective to reduce the incidence of diabetes to less than 40% at 35 weeks of age, as compared to 80% in PBS treated controls.

Example 6

Therapeutic Treatment of Overt IDDM Using DC Electroporated with RNA Encoding IL-4

Figure 8:
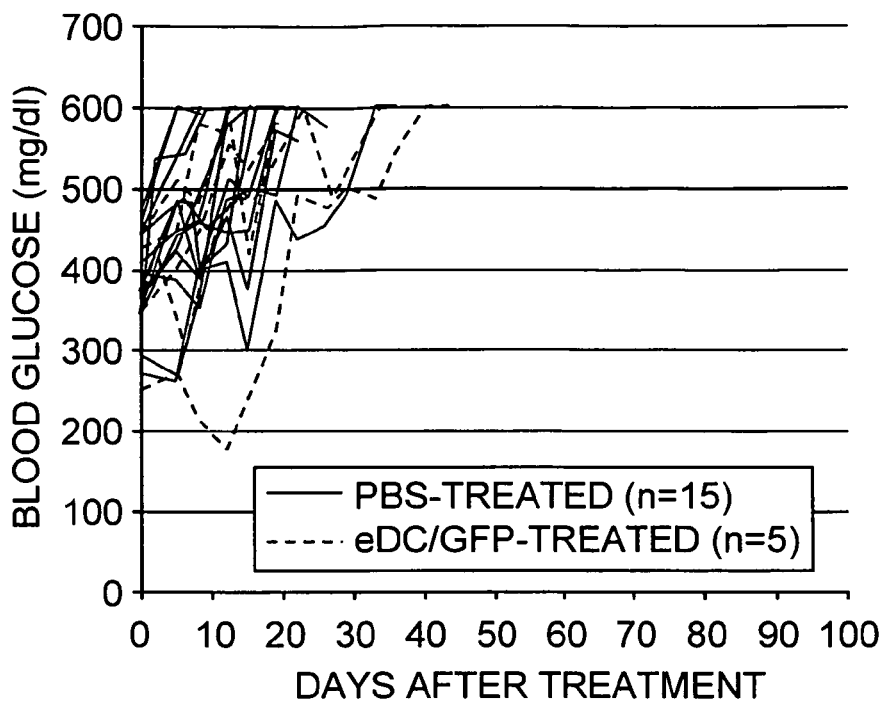
FIG. 8 shows the reversion of hyperglycemia by single injection of fresh or frozen DCs expressing IL-4 via transfected mRNA (eDC/IL-4; bottom graph). Prolonged remission (>2 weeks) was seen in 28% of mice treated with eDC/IL-4, but not in mice treated with either PBS or DCs expressing GFP via transfected mRNA (PBS-treated or eDC/GFP-treated; top graph).
Figure 8:
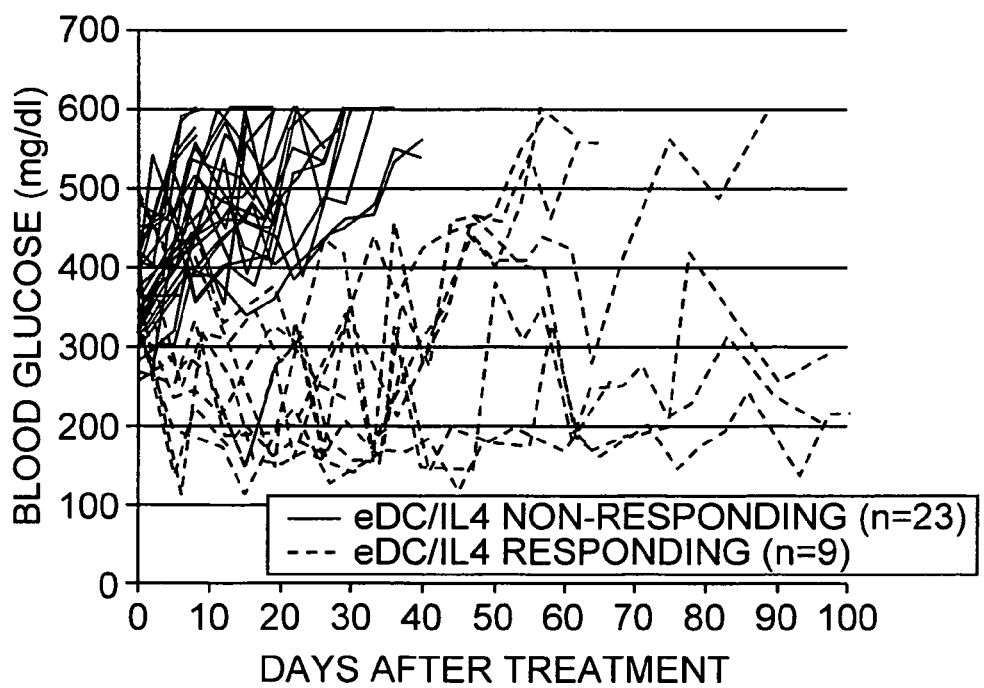

As shown in Example 5, a single injection of DC electroporated with IL-4 encoding RNA significantly reduced the incidence of overt diabetes when administered in the pre-diabetic setting (week 12). However, since human diabetes is typically diagnosed when β cell destruction is well underway, it was important to determine whether the therapeutic potential of eDC/IL-4 in mice already displaying hyperglycemia, and thereby β-cell loss. Accordingly, DC electroporated with IL-4 RNA were administered intravenously on a single occasion ($1 \times 10^6$ DC in 0.2 ml) to animals whose blood glucose level exceed 250 mg/dl at two time points, one or two days apart, prior to therapy. Control mice received either PBS, or DC electroporated with RNA encoding GFP. FIG. 8 shows blood glucose levels over time for individual mice for each cohort. Mice were sacrificed when overtly diabetic (>500 mg/di blood glucose). Normal blood glucose levels are 100-120 mg/dl. Nine of 32 mice treated with DC electroporated with IL-4 encoding RNA showed a stabilization of blood glucose levels, indicating a positive therapeutic intervention, which in some mice exceeded 100 days. Approximately 28% of overtly diabetic mice treated with DCs electroporated with IL-4 RNA achieve a level of glucose control.

We claim:

1. A method for treating an undesired immune response in a patient, comprising: administering to said patient, cells transfected with mRNA encoding an IL-4 receptor agonist, wherein the undesired immune response is an autoimmune disease, wherein said autoimmune disease is insulin dependent diabetes mellitus.

2. The method of claim 1, wherein said mRNA encodes IL-4.

3. The method of claim 1, wherein said cells are co-transfected with mRNA encoding a homing polypeptide.

4. The method of claim 1, wherein said cells selectively accumulate in one or more secondary lymphoid tissues at or proximate to the site of the undesired immune response.

5. The method of claim 1, wherein the cells are dendritic cells.

6. A method for treating an undesired immune response in a patient, comprising: administering to said patient, cells transfected with mRNA encoding an IL-4 receptor agonist, wherein the undesired immune response is the presence of an anti-islet cell antibody in said patient.

7. The method of claim 6, wherein said anti-islet cell antibody is specific for glutamate decarboxylase (GAD), insulinoma associated peptide-2 (IA-2) or insulin.

8. The method of claim 1, wherein said administration is intravenous, intraperitoneal, subcutaneous, intradermal, intramuscular or intranodal.

9. The method of claim 1, wherein the cell expresses a heterologous homing polypeptide.

* * * * *